US008958613B2

(12) United States Patent
Kondo et al.

(10) Patent No.: US 8,958,613 B2
(45) Date of Patent: Feb. 17, 2015

(54) SIMILAR CASE SEARCHING APPARATUS AND SIMILAR CASE SEARCHING METHOD

(75) Inventors: Kenji Kondo, Kyoto (JP); Kazutoyo Takata, Osaka (JP); Kazuki Kozuka, Osaka (JP)

(73) Assignee: Panasonic Corporation, Osaka (JP)

( * ) Notice: Subject to any disclaimer, the term of this patent is extended or adjusted under 35 U.S.C. 154(b) by 395 days.

(21) Appl. No.: 13/482,129

(22) Filed: May 29, 2012

(65) Prior Publication Data
US 2013/0114867 A1 May 9, 2013

Related U.S. Application Data

(63) Continuation of application No. PCT/JP2011/006161, filed on Nov. 4, 2011.

(51) Int. Cl.
G06K 9/00 (2006.01)
G06F 19/00 (2011.01)
G06K 9/68 (2006.01)
G06K 9/62 (2006.01)

(52) U.S. Cl.
CPC .......... *G06K 9/6885* (2013.01); *G06F 19/3443* (2013.01); *G06F 19/321* (2013.01); *G06K 9/623* (2013.01)
USPC ....................................... 382/128

(58) Field of Classification Search
None
See application file for complete search history.

(56) References Cited

U.S. PATENT DOCUMENTS

2004/0003001 A1* 1/2004 Shimura .................... 707/104.1
2010/0232661 A1 9/2010 Hisanaga et al.

FOREIGN PATENT DOCUMENTS

| JP | 2009-045121 | 3/2009 |
| JP | 2010-211749 | 9/2010 |
| JP | 2011-048672 | 3/2011 |

(Continued)

OTHER PUBLICATIONS

Worring, Marcel, Arnold Smeulders, and Simone Santini. "Interaction in content-based image retrieval: An evaluation of the state-of-the-art." Advances in Visual Information Systems. Springer Berlin Heidelberg, 2000. 26-36.*

(Continued)

*Primary Examiner* — Stephen R Koziol
*Assistant Examiner* — Raphael Schwartz
(74) *Attorney, Agent, or Firm* — Wenderoth, Lind & Ponack, LLP.

(57) ABSTRACT

A similar case searching apparatus comprises: an image feature extracting unit; an image interpretation item fitting degree calculating unit which calculates the fitting degree of each image feature quantity to each of image interpretation items, based on first image interpretation knowledge indicating the range of values of image feature quantities of each type; an image interpretation item selecting unit; a weight determining unit which determines the weight to each image feature quantity based on second image interpretation knowledge defining correlations between image feature quantities, such that the weight is larger as the correlation with the image interpretation item is higher; a similar case searching unit which searches for the similar case data items, by adding the determined weight to each image feature quantity of the interpretation target image and a corresponding image feature quantity of the medical images in a case database, and comparing the weighted image feature quantities.

12 Claims, 31 Drawing Sheets

(56) References Cited

FOREIGN PATENT DOCUMENTS

| JP | 2011-118540 | 6/2011 |
|----|-------------|--------|
| JP | 2011-118543 | 6/2011 |

OTHER PUBLICATIONS

Müller, Henning, et al. "A review of content-based image retrieval systems in medical applications—clinical benefits and future directions." International journal of medical informatics 73.1 (2004): 1-23.*

International Search Report issued Dec. 6, 2011 in parent application International Application No. PCT/JP2011/006161.

Jennifer G. Dy et al., "Unsupervised Feature Selection Applied to Content-Based Retrieval of Lung Images", IEEE Transactions on Pattern Analysis and Machine Intelligence, vol. 25, No. 3, Mar. 2003.

Mitsutaka Nemoto et al., "Improvement of Tumor Detection Performance in Mammograms by Feature Selection from a Large Number of Features and Proposal of Fast Feature Selection Method", IEICE Transactions on Information and Systems, D-II, vol. J88-D-II, No. 2, Feb. 2005, pp. 416-426, with partial English translation.

Misato Tamura et al., "Improvement of an extraction method of liver regions based on gray pattern of abnormal regions (2nd Report) ", The Institute of Electronics, Information and communication Engineers, Technical Report of IEICE, Iyougazo, 104 (580), pp. 7-12, Jan. 2005.

Junya Nakagawa et al., "Development of an automated extraction method for liver tumors in three dimensional abdominal CT images", The Institute of Electronics, Information and communication Engineers, Technical Report of IEICE, Sep. 2002.

MeCab (http://mecab.sourceforge.net), Sep. 27, 2009.

ChaSen (http://chasen-legacy.sourceforge.jp), Oct. 13, 2007.

KNP (http://nlp.kuee.kyoto-u.ac.jp/nl-resource/knp.html), Oct. 6, 2011.

CaboCha (http://chasen.org/~taku/software/cabocha/), Jun. 2001.

Naoki Kato et al., "Data Mining and its Applications", Asakura Publishing Co., Ltd., Sep. 25, 2008.

* cited by examiner

FIG. 4

| Early stain is observed in liver segment S3 and washout is observed in late phase, therefore hepatocellular carcinoma is suspicious. |
|---|

FIG. 5

| Image interpretation item |
|---|
| Early stain |
| Washout |

| Disease name |
|---|
| Hepatocellular carcinoma |

FIG. 6

| Image interpretation item | Location | Time phase |
|---|---|---|
| Early stain | Liver segment S3 | — |
| Washout | — | Late phase |

| Disease name |
|---|
| Hepatocellular carcinoma |

FIG. 7

| Image interpretation item | Location | Time phase |
|---|---|---|
| Early stain | Liver segment S3 | Early phase |
| Washout | Liver segment S3 | Late phase |

| Disease name |
|---|
| Hepatocellular carcinoma |

FIG. 8

| Case number | | Lesion number | Feature quantity number | Value |
|---|---|---|---|---|
| 1 | Image feature quantity | (1, 1) | 1 | 0.851 |
| | | | 2 | 0.941 |
| | | | ⋮ | ⋮ |
| | | | $N_{IF}$ | 0.066 |
| | | (1, 2) | 1 | 0.515 |
| | | | 2 | 0.050 |
| | | | ⋮ | ⋮ |
| | | | $N_{IF}$ | 0.593 |
| | | ⋮ | 1 | 0.540 |
| | | | 2 | 0.487 |
| | | | ⋮ | ⋮ |
| | | | $N_{IF}$ | 0.152 |
| | | (1, $M_1$) | 1 | 0.366 |
| | | | 2 | 0.895 |
| | | | ⋮ | ⋮ |
| | | | $N_{IF}$ | 0.073 |
| | Image interpretation item | | (1, 1) | Early stain |
| | | | (1, 2) | Washout |
| | | | ⋮ | ⋮ |
| | | | (1, $N_1$) | High absorption |
| | Disease name | | | Hepatocellular carcinoma |
| ⋮ | | | | |
| C | Image feature quantity | (C, 1) | 1 | 0.703 |
| | | | 2 | 0.975 |
| | | | ⋮ | ⋮ |
| | | | $N_{IF}$ | 0.564 |
| | | (C, 2) | 1 | 0.104 |
| | | | 2 | 0.013 |
| | | | ⋮ | ⋮ |
| | | | $N_{IF}$ | 0.728 |
| | | ⋮ | 1 | 0.893 |
| | | | 2 | 0.489 |
| | | | ⋮ | ⋮ |
| | | | $N_{IF}$ | 0.150 |
| | | (C, $M_C$) | 1 | 0.317 |
| | | | 2 | 0.077 |
| | | | ⋮ | ⋮ |
| | | | $N_{IF}$ | 0.494 |
| | Image interpretation item | | (C, 1) | High absorption |
| | | | (C, 2) | Early stain |
| | | | ⋮ | ⋮ |
| | | | (C, $N_C$) | Afferent |
| | Disease name | | | Angioma |

FIG. 11

| Image interpretation item | Lesion number | Value in each dimension of image feature quantity vector | | | | |
|---|---|---|---|---|---|---|
| | | 1 | 2 | 3 | ... | NIF |
| 1 | 1 | 0.781 | 0.979 | 0.554 | ... | 0.454 |
| | 2 | 0.035 | 0.608 | 0.322 | ... | 0.092 |
| | ... | ... | ... | ... | ... | ... |
| | NF1 | 0.103 | 0.154 | 0.973 | ... | 0.342 |
| 2 | 1 | 0.527 | 0.163 | 0.786 | ... | 0.838 |
| | 2 | 0.233 | 0.626 | 0.955 | ... | 0.456 |
| | ... | ... | ... | ... | ... | ... |
| | NF2 | 0.705 | 0.879 | 0.018 | ... | 0.923 |
| | | | | | | |
| NII | 1 | 0.977 | 0.189 | 0.235 | ... | 0.276 |
| | 2 | 0.803 | 0.321 | 0.970 | ... | 0.438 |
| | ... | | | | ... | ... |
| | NFNII | 0.956 | 0.705 | 0.717 | | 0.064 |

FIG. 16

| | Image feature quantity 1 | Image feature quantity 2 | Image feature quantity 3 | ... | Image feature quantity $N_{IF}$ |
|---|---|---|---|---|---|
| Image interpretation item 1 | 0.808 | 0.627 | 0.973 | ... | 0.304 |
| Image interpretation item 2 | 0.372 | 0.991 | 0.135 | ... | 0.782 |
| Image interpretation item 3 | 0.859 | 0.326 | 0.073 | ... | 0.152 |
| ... | ... | ... | ... | ... | ... |
| Image interpretation item $N_{II}$ | 0.166 | 0.237 | 0.576 | ... | 0.724 |

FIG. 17

| | Image feature quantity 1 | Image feature quantity 2 | Image feature quantity 3 | ... | Image feature quantity $N_{IF}$ |
|---|---|---|---|---|---|
| Disease name 1 | 0.671 | 0.697 | 0.298 | ... | 0.191 |
| Disease name 2 | 0.726 | 0.062 | 0.970 | ... | 0.785 |
| Disease name 3 | 0.365 | 0.129 | 0.085 | ... | 0.695 |
| ... | ... | ... | ... | ... | ... |
| Disease name $N_D$ | 0.277 | 0.238 | 0.897 | | 0.818 |

FIG. 18

| | Disease name 1 | Disease name 2 | Disease name 3 | ... | Disease name $N_D$ |
|---|---|---|---|---|---|
| Image interpretation item 1 | 23.06 | 47.58 | 9.58 | ... | 5.10 |
| Image interpretation item 2 | 1.41 | 6.21 | 32.96 | ... | 12.80 |
| Image interpretation item 3 | 0.95 | 9.80 | 3.94 | ... | 42.18 |
| ... | ... | ... | ... | ... | ... |
| Image interpretation item $N_{II}$ | 36.35 | 22.52 | 16.82 | ... | 23.94 |

FIG. 22

| Image interpretation item | Lesion number | Value in each dimension of image feature quantity vector | | | | |
|---|---|---|---|---|---|---|
| | | 1 | 2 | 3 | ... | NIF |
| 1 | 1 | 0.922 | 0.580 | 0.854 | ... | 0.298 |
| | 2 | 0.631 | 0.121 | 0.523 | ... | 0.980 |
| | ... | ... | ... | ... | ... | ... |
| | NF1 | 0.348 | 0.646 | 0.158 | ... | 0.618 |
| 2 | 1 | 0.407 | 0.220 | 0.729 | ... | 0.854 |
| | 2 | 0.046 | 0.308 | 0.867 | ... | 0.984 |
| | ... | ... | ... | ... | ... | ... |
| | NF2 | 0.303 | 0.021 | 0.632 | ... | 0.736 |
| ... | | | | | | |
| NII | 1 | 0.773 | 0.087 | 0.514 | ... | 0.455 |
| | 2 | 0.909 | 0.085 | 0.970 | ... | 0.158 |
| | ... | ... | ... | ... | ... | ... |
| | NFNII | 0.782 | 0.966 | 0.597 | ... | 0.426 |

FIG. 23

| Image interpretation item | Image feature quantity | |
|---|---|---|
| | Image feature quantity number | Distribution parameter |
| 1 | 1 | $(p_1, p_2, ..., p_{dim})$ |
| | 2 | $(p_1, p_2, ..., p_{dim})$ |
| | ⋮ | ⋮ |
| | NIF1' | $(p_1, p_2, ..., p_{dim})$ |
| 2 | 1 | $(p_1, p_2, ..., p_{dim})$ |
| | 2 | $(p_1, p_2, ..., p_{dim})$ |
| | ⋮ | ⋮ |
| | NIF2' | $(p_1, p_2, ..., p_{dim})$ |
| ⋮ | | |
| NII | 1 | $(p_1, p_2, ..., p_{dim})$ |
| | 2 | $(p_1, p_2, ..., p_{dim})$ |
| | ⋮ | ⋮ |
| | NIFNII' | $(p_1, p_2, ..., p_{dim})$ |

FIG. 24

| Image interpretation item | Distribution parameter |
|---|---|
| 1 | $(p_1, p_2, ..., p_{dim})$ |
| 2 | $(p_1, p_2, ..., p_{dim})$ |
| ⋮ | |
| NII | $(p_1, p_2, ..., p_{dim})$ |

FIG. 25

| Image interpretation item |
|---|
| Early stain<br>Patchy<br>Homogenous inside<br>Ring-shaped<br>... |

FIG. 26

Simple phase image     Early phase image     Equilibrium phase image

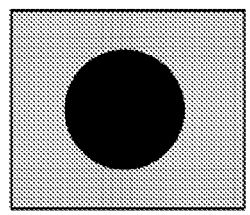 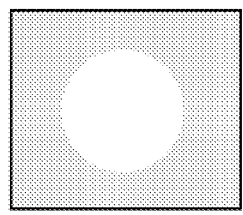 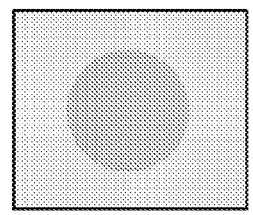

| Image interpretation item |
|---|
| Low absorption<br>Unclear border<br>... |

| Image interpretation item |
|---|
| Early stain<br>Patchy<br>Homogenous inside<br>Ring-shaped<br>... |

| Image interpretation item |
|---|
| Washout<br>Unclear border<br>Low density<br>... |

FIG. 27

| Image interpretation item | Fitting degree |
|---|---|
| Early stain | 0.84 |
| Patchy | 0.71 |
| Homogenous inside | 0.60 |
| Ring-shaped | 0.21 |
| ... | ... |

FIG. 28

| Image interpretation item | Fitting degree |
|---|---|
| Early stain | ▨▨▨▨▨▨▨▨ |
| Patchy | ▨▨▨▨▨▨▨ |
| Homogenous inside | ▨▨▨▨▨▨ |
| Ring-shaped | ▨▨ |
| ... | ... |

FIG. 29

| Image interpretation item |
|---|
| Early stain |
| Patchy |
| Homogenous inside |
| Ring-shaped |
| ... |

FIG. 31

| Image interpretation item | Weight adjustment for similar case search |
|---|---|
| Early stain<br>Patchy<br>Washout<br>Homogenous inside<br>Ring-shaped<br>... | Small ——————□———— Large<br>Small ——————————□—— Large |

FIG. 32

|  | Image interpretation item 1 | Image interpretation item 2 | Image interpretation item 3 | ... | Image interpretation item $N_{II}$ |
|---|---|---|---|---|---|
| Image interpretation item 1 | | 0.627 | 0.973 | ... | 0.304 |
| Image interpretation item 2 | | | 0.135 | ... | 0.782 |
| Image interpretation item 3 | | | | ... | 0.152 |
| ... | | | | | ... |
| Image interpretation item $N_{II}$ | | | | | |

FIG. 41

| Priority order | Image interpretation item | Selection flag |
|---|---|---|
| 1 | Early stain | 1 |
| 2 | Patchy | 0 |
| 3 | Washout | 1 |
| 4 | Homogenous inside | 0 |
| 5 | Ring-shaped | 0 |

US 8,958,613 B2

SIMILAR CASE SEARCHING APPARATUS AND SIMILAR CASE SEARCHING METHOD

CROSS REFERENCE TO RELATED APPLICATION

This is a continuation application of PCT Patent Application No. PCT/W2011/006161 filed on Nov. 4, 2011, designating the United States of America. The entire disclosure of the above-identified application, including the specification, drawings and claims are incorporated herein by reference in its entirety.

TECHNICAL FIELD

Apparatuses and methods consistent with one or more exemplary embodiments of the present disclosure relate generally to similar case searching apparatuses and similar case searching methods for searching out a similar case that is useful as a reference for an interpretation of an image for medical use (medical image).

BACKGROUND ART

Recent development and wide spread use of medical imaging apparatuses for Computed Tomography (CT) and Magnetic Resonance Imaging (MRI) have made it possible to obtain a large volume of high-definition digital images for medical use. Furthermore, medical images already interpreted by doctors are increasingly accumulated one by one together with the image interpretation reports thereof in Picture Archiving and Communication Systems (PACS). In order to interpret a target image with reference to medical images similar to the target image, a start is made for development of techniques for searching out the similar images (medical images) from already-accumulated past cases.

In a similar image search, it is important to optimize image feature quantities for determining a similarity between images according to a current target image for the similar image search. Conventionally, image feature quantities are designed for each of target organs for which similar image searches are performed. In most of similar image searches, the same image feature quantities are used in common to concept levels other than such organs (examples of such concept levels include the kinds of diseases, the progress (stages) of the diseases or the seriousness of the diseases).

As a similar image search method for dynamically changing image feature quantities to be used in a similar image search according to concept levels other than an organ, the following technique is disclosed.

Non-patent Literature 1 proposes a searching approach composed of two steps that are "Customized-Queries" Approach (CQA) as a means for solving the problem. The first step of this approach is to classify query images using image feature quantities for classifying classes of the kinds of diseases, the progress of the diseases or the seriousness of the diseases, and the like in the optimum manner. The second step of this approach is to search similar images using the image feature quantities optimized for further classifying the cases included in each of the classes obtained as a result of the previous classification. At this time, the image feature quantities optimum for the classes are calculated in advance through unsupervised learning. Furthermore, the technique disclosed in the Non-patent Literature applies CQA for a lung CT images and to thereby achieve a search recall factor increased from those obtainable in such conventional similar image search using only a single kind of image feature quantities.

CITATION LIST

Non Patent Literature

[NPL 1]
Jennifer G. Dy et al. "Unsupervised Feature Selection Applied to Content-based Retrieval of Lung Images", IEEE Transactions on Pattern Analysis and Machine Intelligence, vol. 25, no. 3, March 2003

SUMMARY OF INVENTION

Technical Problem

However, the apparatus in Non-patent Literature 1 cannot perform a similar image search in which doctor focus points on the target image are reflected.

Solution to Problem

The similar case searching apparatus according to one or more exemplary embodiments of the present disclosure reflects the user (such as a doctor) focus points on a similar image search. One or more exemplary embodiments of the present disclosure may overcome the above disadvantage(s) and other disadvantages not described herein. However, it is understood that one or more exemplary embodiments of the present disclosure are not required to overcome or may not overcome the disadvantage(s) described above and other disadvantages not described herein.

A similar case searching apparatus according to an aspect of the present disclosure is a similar case searching apparatus which searches a case database for similar case data items including similar images similar to an interpretation target image, the case database storing a plurality of case data items, and each of the plurality of case data items and a case data item of the interpretation target image including one or more medical images and an image interpretation report that is a document data item indicating interpretations of the medical images. The similar case searching apparatus comprises: an image feature quantity extracting unit configured to extract a plurality of image feature quantities from one of the medical images that is the interpretation target image; an image interpretation item fitting degree calculating unit configured to calculate a fitting degree of the image feature quantities extracted by the image feature quantity extracting unit with respect to each of image interpretation items, based on first image interpretation knowledge composed of information items each indicating a presence range of values of image feature quantities of a corresponding type extracted from medical images whose image interpretation reports include the image interpretation item, each of the image interpretation items being a character string verbally indicating a feature of the medical images, the information items being prepared for the respective image interpretation items; and the values being calculated with respect to each of the image interpretation items; an image interpretation item candidate display unit configured to display one of (a) image interpretation items each having a fitting degree larger than a predetermined threshold value and (b) a predetermined number of image interpretation items selected in a descending order of their fitting degrees, both (a) and (b) being included in the image interpretation items; an image interpretation item selecting unit configured to allow a user to select one or more of the image interpretation items displayed by the image interpretation item candidate display unit; a weight determining unit configured to determine, based on second image interpretation knowledge, a weight that is added to each of the image feature quantities extracted by the image feature extracting unit, such that the weight to the image feature quantity is larger as a correlation between the image feature quantity and the one of the image interpretation items selected by the image interpretation item selecting unit is higher, the second image interpretation knowledge being prepared information defining correlations between image feature quantities extracted from medical images and image interpretation items selected from the image interpretation reports of the medical images; and a similar case searching unit configured to search the case database for the similar case data items, by weighting each of the image feature quantities in a first set extracted from the interpretation target image by the image feature quantity extracting unit and a corresponding one of the image feature quantities in a second set extracted from the medical images included in the case data items registered in the case database, using the weight to the image feature quantity determined by the weight determining unit, and comparing the weighted image feature quantities in the first set and the weighted image feature quantities in the second set.

It is to be noted that each of general or specific embodiments of the present disclosure may be implemented or realized as a system, a method, an integrated circuit, a computer program, or a recording medium, and that (each of) the specific embodiments may be implemented or realized as an arbitrary combination of (parts of) a system, a method, an integrated circuit, a computer program, or a recording medium.

Advantageous Effects of Invention

According to various exemplary embodiments of the present disclosure, it is possible to provide similar case searching apparatuses capable of reflecting user focus points on similar image searches.

BRIEF DESCRIPTION OF DRAWINGS

These and other advantages and features of exemplary embodiments of the present disclosure will become apparent from the following description thereof taken in conjunction with the accompanying Drawings that illustrate general and specific exemplary embodiments of the present disclosure. In the Drawings:

FIG. 4 is a diagram showing an example of an image interpretation report regarding an abdominal CT scan according to Embodiment 1;

FIG. 5 is a table of image interpretation items and a disease name extracted from the image interpretation report according to Embodiment 1;

FIG. 6 is a table of image interpretation items and a disease name extracted from the image interpretation report according to Embodiment 1, and positions and time phases extracted together with the image interpretation items;

FIG. 7 is a table of image interpretation items and a disease name extracted from the image interpretation report according to Embodiment 1, and positions and time phases extracted together with the image interpretation items by performing context interpretation;

FIG. 8 is a table of a set of data items obtained for the extraction of image interpretation knowledge according to Embodiment 1;

FIG. 11 is a table (a storage format) of distribution information that indicates image feature quantities that corresponds to the given image interpretation item and is the first image interpretation knowledge according to Embodiment 1;

FIG. 16 is a table (a storage format) of correlations between image feature quantities and image interpretation items extracted as image interpretation knowledge according to Embodiment 1;

FIG. 17 is a table (a storage format) of correlations (between image feature quantities and disease names) extracted as image interpretation knowledge according to Embodiment 1;

FIG. 18 is a table (a storage format) of correlations (between image interpretation items and disease names) extracted as image interpretation knowledge according to Embodiment 1;

FIG. 22 is a table (a storage format) of distribution information that indicates image feature quantities that corresponds to the given image interpretation item and is the first image interpretation knowledge according to Embodiment 1;

FIG. 23 is a table (a storage format) of distribution information that indicates image feature quantities that corresponds to the given image interpretation item and is the first image interpretation knowledge according to Embodiment 1;

FIG. 24 is a table (a storage format) of distribution information that indicates image feature quantities that corresponds to the given image interpretation item and is the first image interpretation knowledge according to Embodiment 1;

FIG. 25 is a table (a display format) of image interpretation items each determined to have a large fitting degree according to Embodiment 1;

FIG. 26 is composed of pairs of an image and a table (a display format) of sets of image interpretation items each determined to have a large fitting degree according to Embodiment 1;

FIG. 27 is a table (a display format) of image interpretation items determined to have large fitting degrees and the fitting degrees displayed at the same time according to Embodiment 1;

FIG. 28 is a table (a display format) of image interpretation items determined to have large fitting degrees and the fitting degrees displayed at the same time according to Embodiment 1;

FIG. 29 is a table (a display format) of image interpretation items including an image interpretation item selected by a user according to Embodiment 1;

FIG. 31 is an illustration of an example of an image screen for allowing the user to set weights to image interpretation items using a slide bar in a similar case search according to Embodiment 1;

FIG. 32 is a table of correlations between image feature quantities extracted as image interpretation knowledge according to Embodiment 2 of the present disclosure;

FIG. 41 is a table of an example of selection history information of image interpretation items stored in an, image interpretation item selection history database according to Embodiment 6.

DESCRIPTION OF EMBODIMENTS

Figure 1:
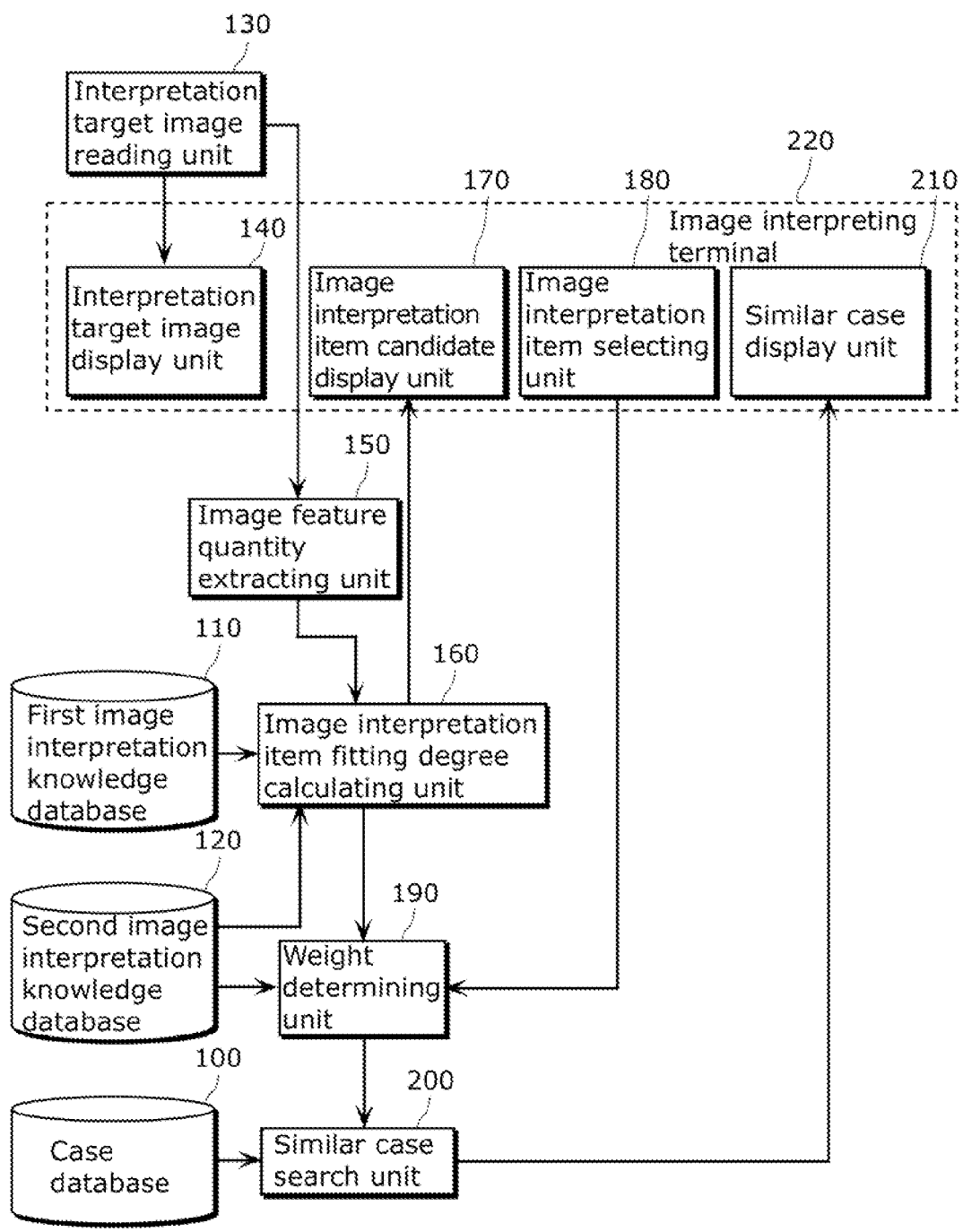
FIG. 1 is a block diagram of a structure of a similar case searching apparatus according to Embodiment 1 of the present disclosure.

Underlying Knowledge Forming Basis of the Present Disclosure

The inventors have found that the searching method proposed in Non-patent Literature (NPL) 1 described in the section of "Background Art" has disadvantages described below.

The method in NPL 1 is merely intended to determine image feature quantities (that are the reference for similarity determinations) based on the identified kinds of the diseases and the identified progress or seriousness of the diseases, and the like, and search out similar images using the determined image feature quantities. Thus, the method does not enable a similar image search in which user's focus points on the target medical image are reflected. The indicators (focus points) for determining the similarities between images are various even when the images are of a particular type. Examples of the indicators include, the shape, the luminance, the whole area, and a partial area. Only a user who performs a similar image search knows which indicator is expected in a search for a "similar" image.

In other words, if a medical image is searched for using image feature quantities previously optimized based on the identified kinds of the diseases and the identified progress or seriousness of the diseases, and the like, the searched-out image is less likely to be useful to find a basis of a diagnosis made by the user or help the user who has difficulty in making a diagnosis to make a diagnosis.

In order to solve the aforementioned problem, a similar case searching apparatus according to an aspect of the present disclosure is a similar case searching apparatus which searches a case database for similar case data items including similar images similar to an interpretation target image, the case database storing a plurality of case data items, and each of the plurality of case data items and a case data item of the interpretation target image including one or more medical images and an image interpretation report that is a document data item indicating interpretations of the medical images. The similar case searching apparatus comprises: an image feature quantity extracting unit configured to extract a plurality of image feature quantities from one of the medical images that is the interpretation target image; an image interpretation item fitting degree calculating unit configured to calculate a fitting degree of the image feature quantities extracted by the image feature quantity extracting unit with respect to each of image interpretation items, based on first image interpretation knowledge composed of information items each indicating a presence range of values of image feature quantities of a corresponding type extracted from medical images whose image interpretation reports include the image interpretation item, each of the image interpretation items being a character string verbally indicating a feature of the medical images, the information items being prepared for the respective image interpretation items, and the values being calculated with respect to each of the image interpretation items; an image interpretation item candidate display unit configured to display one of (a) image interpretation items each having a fitting degree larger than a predetermined threshold value and (b) a predetermined number of image interpretation items selected in a descending order of their fitting degrees, both (a) and (b) being included in the image interpretation items; an image interpretation item selecting unit configured to allow a user to select one or more of the image interpretation items displayed by the image interpretation item candidate display unit; a weight determining unit configured to determine, based on second image interpretation knowledge, a weight that is added to each of the image feature quantities extracted by the image feature extracting unit, such that the weight to the image feature quantity is larger as a correlation between the image feature quantity and the one of the image interpretation items selected by the image interpretation item selecting unit is higher, the second image interpretation knowledge being prepared information defining correlations between image feature quantities extracted from medical images and image interpretation items selected from the image interpretation reports of the medical images; and a similar case searching unit configured to search the case database for the similar case data items, by weighting each of the image feature quantities in a first set extracted from the interpretation target image by the image feature quantity extracting unit and a corresponding one of the image feature quantities in a second set extracted from the medical images included in the case data items registered in the case database, using the weight to the image feature quantity determined by the weight determining unit, and comparing the weighted image feature quantities in the first set and the weighted image feature quantities in the second set.

With this structure, the similar case searching apparatus calculates the fitting degree of each of the image feature quantities extracted from the interpretation target image and the similar images with respect to each of the "image interpretation items", so as to transform disease based information about the feature of the interpretation target image into image interpretation item based information that is of a level finer than the level of the disease based information. The use of the finer information makes it possible to perform optimization of the image feature quantities for a search at the finer level.

An "image interpretation item" is defined in this Description as a "character string made by a doctor as verbally indicating a feature of an interpretation target image". Terms that are used as image interpretation items are limited within certain ranges for the respective medial-use imaging apparatuses, target organs, or the like. Examples of the image interpretation items include: Lobular, Spinal, Irregular, Clear border, Unclear contour, Low density, High density, Low absorption, High absorption, Ground-glass opacity, Calcification, Mosaic pattern, Early stain, Low echo, High echo, and Fuzz. For example, it is known that the user is focused on the shape of a lesion when the selected image interpretation item is one of Lobular, Spinal, and Irregular, and that the user is focused on the luminance of a lesion when the selected image interpretation item is one of Low density, High density, Low absorption, High absorption, and Ground-glass opacity.

At the same time, such image interpretation items are a language commonly used when doctors generate image interpretation reports, and thus the user (image interpreter) of the similar case searching apparatus can easily understand the validities of the image interpretation items estimated by the similar case searching apparatus.

Furthermore, the similar case searching apparatus displays the image interpretation items having a large fitting degree, more specifically, displays the image interpretation items strictly selected as being related to the image feature quantities extracted from the interpretation target image from among the numerous image interpretation items. Thus, the user of the similar case searching apparatus can easily recognize and select the one or more of the displayed image interpretation items.

In this way, it is possible to perform similar case searches in which the focus points by the user (image interpreter) of the similar case searching apparatus are reflected.

For example, the image interpretation item fitting degree calculating unit may be configured to: obtain, from the first image interpretation knowledge, a presence range information item indicating values of all of the image feature quantities related to each of target image interpretation items with respect to which the fitting degrees are calculated; calculate matching degrees of the respective image feature quantities extracted by the image feature quantity extracting unit with respect to the obtained presence range information item; and calculate the fitting degree of the image feature quantities extracted by the image feature quantity extracting unit with respect to each of the target image interpretation items, by (i) weighting the image feature quantity using a weight calculated with respect to the matching degree of the image feature quantity such that the weight to the image feature quantity is larger as the image feature quantity is determined, based on the second image interpretation knowledge, to be more highly related to the target image interpretation item, and (ii) integrating the matching degrees calculated for the image feature quantities extracted by the image feature quantity extracting unit.

With this structure, the similar case searching apparatus calculates the fitting degree by reducing the influence of image feature quantities having a low correlation with one of the image interpretation items even in the state where various kinds of image feature quantities are present.

In addition, the image interpretation item candidate display unit may be further configured to display the fitting degrees with respect to the image interpretation items, together with the image interpretation items.

With this structure, the similar case searching apparatus presents, to the user, information about the magnitudes of the calculated fitting degrees of the image interpretation items. Thus, the user can utilize the information in the selection of the image interpretation items.

In addition, the image interpretation item candidate display unit may further be configured to: determine a co-occurrence probability of each of pairs of the image interpretation items selected by the image interpretation item selecting unit, based on prepared co-occurrence probability information defining a co-occurrence degree of the pair of the image interpretation items in the image interpretation reports attached to the medical images; and display information indicating a possibility that an inappropriate image interpretation item is included by mistake in one of the pairs having the determined co-occurrence probability when the determined co-occurrence probability is smaller than or equal to a predetermined value.

With this structure, the similar case searching apparatus notifies the user of the pair of the image interpretation items that rarely co-occur, and thereby prevents the user from selecting the pair (especially one of the image interpretation items in the pair).

In addition, the image interpretation item candidate display unit is may further be configured to display, based on the prepared co-occurrence probability information, information indicating that it is impossible to select the image interpretation item having a co-occurrence probability calculated as being smaller than or equal to the predetermined value with respect to one of the image interpretation items selected by the image interpretation item selecting unit, the prepared co-occurrence probability information defining the co-occurrence degrees of the pairs of the image interpretation items included in the image interpretation reports attached to the medical images.

With this structure, the similar case searching apparatus notifies the user of the pair of the image interpretation items one of which cannot be selected together with the other when the pair is selected, and thereby prevents the user from selecting the one which cannot be selected.

In addition, the image interpretation item candidate display unit may further be configured to: estimate a disease name having a highest correlation with each of the selected image interpretation items, based on correlation information extracted from the image interpretation reports attached to the medical images, the correlation information being prepared as information defining correlations between disease names and image interpretation items each of which is a character string verbally indicating a feature of medical images; and display the estimated disease name.

With this structure, the similar case searching apparatus notifies the user of supplemental information about what disease relates to the currently being selected image interpretation item. Thus, the user can utilize the supplemental information in the determination of the validity of the selected image interpretation item.

A similar case searching apparatus according to another aspect of the present disclosure is a similar case searching apparatus which searches a case database for similar case data items including similar images similar to an interpretation target image, the case database storing a plurality of case data items, and each of the plurality of case data items and a case data item of the interpretation target image including one or more medical images and an image interpretation report that is a document data item indicating interpretations of the medical images, the similar case searching apparatus comprising: an image feature quantity extracting unit configured to extract a plurality of image feature quantities from one of the medical images that is the interpretation target image; an image interpretation item fitting degree calculating unit configured to calculate a fitting degree of the image feature quantities extracted by the image feature quantity extracting unit with respect to each of image interpretation items, based on first image interpretation knowledge composed of information items each indicating a presence range of values of image feature quantities of a corresponding type extracted from medical images whose image interpretation reports include the image interpretation item, each of the image interpretation items being a character string verbally indicating a feature of the medical images, the information items being prepared for the respective image interpretation items, and the values being calculated with respect to each of the image interpretation items; an image interpretation item setting unit configured to set, as an image interpretation item for use in a similar case search, an image interpretation item having a fitting degree that is a value calculated by the image interpretation item fitting degree calculating unit as being larger than or equal to a predetermined threshold value and; a weight determining unit, configured to determine, based on second image interpretation knowledge, a weight that is added to each of the image feature quantities extracted by the image feature extracting unit, such that the weight to the image feature quantity is larger as a correlation between the image feature quantity and the one of the image interpretation items selected by the image interpretation item selecting unit is higher, the second image interpretation knowledge being prepared information defining correlations between image feature quantities extracted from medical images and image interpretation items selected from the image interpretation reports of the medical images; and a similar case searching unit configured to search the case database for the similar case data items, by weighting each of the image feature quantities in a first set extracted from the interpretation target image by the image feature quantity extracting unit and a corresponding one of the image feature quantities in a second set extracted from the medical images included in the case data items registered in the case database, using the weight to the image feature quantity determined by the weight determining unit, and comparing the weighted image feature quantities in the first set and the weighted image feature quantities in the second set.

With this structure, the similar case searching apparatus searches out a similar case by weighting each of the image feature quantities in the first set extracted from the interpretation target image and the corresponding one of the image feature quantities in the second set extracted from the similar images, such that the weight to the image feature quantity is larger as the correlation between the image feature quantity and the one of the image interpretation items estimated from the interpretation target image is higher, and comparing the weighted first set and the weighted second set. With this structure, the similar case searching apparatus performs the weighting utilizing the image interpretation items that are the focus points by general image interpreters, without requiring the user to select the image interpretation items.

The similar case searching apparatus utilizes the image interpretation items having the fitting degree larger than or equal to the predetermined threshold value in the similar case search. Thus, the similar case searching apparatus can perform a similar case search based on the image interpretation items that would be focused by such general doctors.

For example, the image interpretation item setting unit may select the same image interpretation items as in history information of sets of image interpretation items previously selected by the user, from among the image interpretation items having the fitting degree calculated by the image interpretation item fitting degree calculating unit as being larger than or equal to the predetermined threshold value, and set, as image interpretation items for use in a similar case search, the image interpretation items obtained based on the history information.

With this structure, the user can perform the similar case search using the same image interpretation items as in the image interpretation items previously selected by the user. For this reason, for example, it is possible to perform a similar case search for a new interpretation target image using the same image interpretation items as the image interpretation items selected by a skilled doctor in the past.

It is to be noted that each of the general or specific embodiments of the present disclosure may be implemented or realized as a system, a method, an integrated circuit, a computer program, or a recording medium, and that (each of) the specific embodiments may be implemented or realized as an arbitrary combination of (parts of) a system, a method, an integrated circuit, a computer program, or a recording medium.

Hereinafter, a similar case searching apparatus according to an embodiment of the present disclosure is described in detail with reference to the drawings. Each of the embodiments described below shows an example of the present disclosure. Each of the embodiments described below shows an example of the present disclosure. The numerical values, structural elements, the arrangement and connection of the structural elements, steps, the processing order of the steps etc. shown in the following embodiments are mere examples, and therefore do not limit the scope of the present disclosure the scope of which should be defined by the Claims and the equivalents. Among the structural elements in the following embodiments, the structural elements not recited in any one of the independent Claims defining the most generic concept of the present invention are described as optional structural elements in the embodiments.

Embodiment 1

FIG. 1 is a block diagram of a structure of a similar case searching apparatus according to Embodiment 1 of the present disclosure.

According to an exemplary embodiment of the present disclosure, a similar case searching apparatus searches a case database for a case data including a medical image similar to an interpretation target image. The case database stores sets of accumulated case data items each composed of a medical image and an image interpretation report that is a document data item describing the result of the interpretation of the medical image. The similar case searching apparatus comprising: a case database 100, a first image interpretation knowledge database 110, a second image interpretation knowledge database 120, an interpretation target image display unit 130, an interpretation target image display unit 140, an image feature quantity extracting unit 150, an image interpretation item fitting degree calculating unit 160, an image interpretation item candidate display unit 170, an image interpretation item selecting unit 180, a weight determining unit 190, a similar case search unit 200, and a similar case display unit 210. The similar case searching apparatus further comprises an image interpretation report input unit (not shown).

The case database 100 is a database storing a plurality of case data items (hereinafter simply referred to as "cases"). Each of the case data item is composed of pairs of a medical image (in this Description, "image data" is simply referred to as an "image") and an image interpretation report that is the result of interpretation of the medical image). Such a medical image is an image used for Computer Tomography (CT), Magnetic Resonance Imaging (MRI), or the like. Each of the first image interpretation knowledge database 110 and the second image interpretation knowledge database 120 is a database storing image interpretation knowledge obtained by analyzing a plurality of cases. This first image interpretation knowledge database 110 is described in detail later. The case database 100 and the first image interpretation knowledge database 110 and the second image interpretation knowledge database 120 are stored in a recording device such as a Hard Disk Drive (HDD).

The interpretation target image reading unit 130 reads an image captured by a medical image capturing apparatus for CT, MRI, or the like from the medical image capturing apparatus or a storage device connected from outside.

The interpretation target image display unit 140 is composed of a medical-use high-definition monitor or the like, and displays the image interpretation target image read by the interpretation target image reading unit 130.

The image feature quantity extracting unit 150 extracts a plurality of kinds of image feature quantities from the interpretation target image read by the interpretation target image reading unit 130.

The image interpretation item fitting degree calculating unit 160 calculates a fitting degree, with respect to each of image interpretation items, of each of a plurality of image feature quantities in a current interpretation target image, based on the image feature quantities extracted by the image feature quantity extracting unit 150 and the first image interpretation knowledge stored in the first image interpretation knowledge database 110.

The image interpretation item candidate display unit 170 displays, as candidates selectable by the user, image interpretation items having a fitting degree larger than a predetermined threshold value or a predetermined number of image interpretation items selected in the descending order of their fitting degrees, based on the fitting degrees to the respective image interpretation items calculated by the image interpretation item fitting degree calculating unit 160. The user (image interpreter) of the similar case searching apparatus is a doctor such as a radiologist and a clinician who interprets medical images. However, users are not limited to these doctors, and may be a clinical technologist, a medical student, and the like who do not have a doctor's license.

The image interpretation item selecting unit 180 receives, as an input, a user selection selected from image interpretation items displayed by the image interpretation item candidate display unit 170.

The weight determining unit 190 determines weights respectively added to the image feature quantities to be used to search images, based on the image feature quantities extracted by the image feature quantity extracting unit 150, and the second image interpretation knowledge stored in the second image interpretation knowledge database 120.

The similar case search unit 200 searches the case database 100 for a case including a medical image similar to the interpretation target image and registered in the case database 100 by weighting each of pairs of an image feature quantity of a kind extracted by the image feature quantity extracting unit 150 and an image feature quantity of the same kind extracted from the medical image included in the case, using the weight determined by the weight determining unit 190 for the pair of image feature quantities.

The similar case display unit 210 displays the similar case searched out by the similar case search unit 200. The similar case display unit 210 may be separately configured with a device of the same model as that of the high-definition monitor constituting the interpretation target image display unit 140. Furthermore, the interpretation target image and the similar case may be displayed on the high-definition monitor constituting the interpretation target image display unit 140 at the same time. Here, the similar case display unit 210 and the interpretation target image display unit 140 may be different in their device models.

The image interpretation report input unit (not shown) receives, from a user, an input of an image interpretation report. In other words, the user inputs the image interpretation report to the image interpretation report input unit (not shown) with reference to the interpretation target image displayed on the interpretation target image display unit 140 and a similar case displayed by the similar case display unit 210. The image interpretation report input unit is composed of a keyboard, a mouse, and the like.

The interpretation target image display unit 140, the image interpretation item candidate display unit 170, the image interpretation item selecting unit 180, the similar case display unit 210, and the image interpretation report input unit constitute an image interpreting terminal 220.

Hereinafter, operations performed by the respective units of an embodiment of the present disclosure are described in detail.

(Preparation of Image Interpretation Knowledge Database)

Prior to a similar case search, image interpretation knowledge is generated in advance, and is stored in the first image interpretation knowledge database 110 and the second image interpretation knowledge database 120. The image interpretation knowledge is generated to include a plurality of "cases" each of which is composed of pairs of a medical image and the image interpretation report that is obtained as the result of the interpretation of the medical image. The similar case to be searched out and used here may be a case stored in the case database 100, or a case stored in another database. The required number of cases should be a number sufficient to obtain a certain law and knowledge using various kinds of data mining algorithms. The number of data items is normally any number in a range from several hundreds to several tens of thousands. In this embodiment, information used here as the first image interpretation knowledge stored in the first image interpretation knowledge database 110 is information indicating a presence range of values for each kind of image feature quantities calculated based on the image feature quantities extracted from the medical image corresponding to the image interpretation report including a given image interpretation item. In addition, information used here as the second image interpretation knowledge stored in the second image interpretation knowledge database 120 includes correlations between image feature quantities extracted from the medical image and image interpretation items extracted from the image interpretation report corresponding to the medical image. These correlations are correlations between two of three data types, for example correlations indicating the correlations between the image feature quantities and the image interpretation items.

The "image feature quantities" relate to, for example, the shapes of organs or lesion portions in medical images, or the luminance distributions of the medical images. For example, Non-patent Literature 2 describes the use of four hundreds and ninety kinds of feature quantities (Non-patent Literature 2: "Improvement of Tumor Detection Performance in Mammograms by Feature Selection from a Large Number of Features and Proposal of Fast Feature Selection Method", by Nemoto, Shimizu, Hagihara, Obata, and Nawano, The Journal of the Institute of Electronics, Information and Communication Engineers (J. IEICE) D-II, Vol. J88-D-II, No, 2, pp. 416-426, February 2005). As image feature quantities used in this embodiment, several ten to several hundred kinds of image feature quantities are predefined for each of medical imaging apparatuses (modality apparatuses) used to capture the medical images or each of target organs used for image interpretation.

An "image interpretation item" is defined in this Description as a "character string made by a doctor as verbally indicating a feature of an interpretation target image". Terms that are used as image interpretation items are limited to certain ranges for the respective medial imaging apparatuses, target organs, or the like. Examples of the image interpretation items include: Lobular, Spinal, Irregular, Clear border, Unclear contour, Low density, High density, Low absorption, High absorption, Ground-glass opacity, Calcification, Mosaic pattern, Early stain, Low echo, High echo, and Fuzz.

Hereinafter, a procedure for generating the second image interpretation knowledge is described with reference to the flowchart of FIG. 2. It is assumed that the medical imaging apparatus that is used in this embodiment is a multi-slice CT, and that the target organ and a target disease are a liver and a liver tumor, respectively.

In Step S10, a case is obtained from a database storing cases for obtaining image interpretation knowledge. Here, the total number of cases for obtaining the image interpretation knowledge is assumed to be C. A case is composed of pairs of one or more medical images and an image interpretation report obtained as a result of the interpretation of the medical image. When the medical images are obtained by the multi-slice CT apparatus, the case includes several slice images. Normally, when a doctor interprets such multi-slice CT images, one to several important slice images among the slice images are attached to the corresponding image interpretation report as key images. Hereinafter, a set of several slice images or several key images are simply referred to as "medical images" or "images".

In Step S11, image feature quantities are extracted from the medical images. The process in Step S11 is described in detail with reference to the flowchart in FIG. 3.

In Step S111, an area in the target organ is extracted. In this embodiment, an area of a liver is extracted. As a liver area extracting approach, the following approach Can be used: Non-patent Literature 3: "Improvement of an extraction method of liver regions based on gray pattern of abnormal regions (2nd Report)", Tanaka, Shimizu, and Obata, The Technical Report of IEICE, Medical Image, 104 (580), pp. 7-12, January 2005.

In Step S112, a lesion portion is extracted from the organ area extracted in Step S111. In this embodiment, a tumor portion in the liver area is extracted. As an example of a liver tumor portion extracting approach, the following approach can be used: Non-patent Literature 4: "Development of an automated extraction method for liver tumors in three dimensional abdominal CT images (2nd Report)", Nakagawa, Shimizu, Hitosugi, and Kobatake, The Technical Report of IEICE, Medical Image, 102 (575), pp. 89-94, January 2003. Here, assuming that the number of tumors extracted from the images in an i-th case is $M_i$, each of the tumors can be identified as a pair (i, j) where i denotes the case number and j denotes the tumor number. Here, $1 \le i \le C$ and $1 \le j \le M_i$ are satisfied. The name "tumor number" is used because the target lesion in this embodiment is the liver tumor. However, the "tumor number" may be referred to as a "lesion number" that is the common term in this embodiment of the present disclosure.

In Step S113, one of the lesion portions extracted in Step S112 is selected.

In Step S114, an image feature quantity is extracted from the lesion portion selected in Step S113. In this embodiment, some feature quantities applicable for the liver tumor are selected, for use, from among the four hundreds and ninety kinds of image feature quantities described in Non-patent Literature 2: "Improvement of Tumor Detection Performance in Mammograms by Feature Selection from a Large Number of Features and Proposal of Fast Feature Selection Method", by Nemoto, Shimizu, Hagihara, Kobatake, and Nawano, The Journal of the Institute of Electronics, Information and Communication Engineers (J. IEICE) D-II, Vol. J88-D-II, No, 2, pp. 416-426, February 2005). The number of these feature quantities is assumed to be NF. The feature quantities extracted in this step can be identified as a set (i, j, k) where i denotes the case number, j denotes the tumor number extracted from this case (medical image), and k denotes the feature number. Here, $1 \le i \le C$, $1 \le j \le M_i$, and $1 \le k \le N_F$ are satisfied.

In Step S115, a check is made to detect whether or not any unselected lesion portion remains among the lesion portions extracted in Step S112. When an unselected lesion portion remains, a return is made to Step S113 and the unselected lesion portion is selected and then Step S114 is executed again. When no unselected lesion portion remains, in other words, when a feature quantity selection in Step S114 is already made for all the lesion portions extracted in Step S112, the processes in the flowchart in FIG. 3 are completed, and a return is made to the flowchart in FIG. 2.

Figure 2:
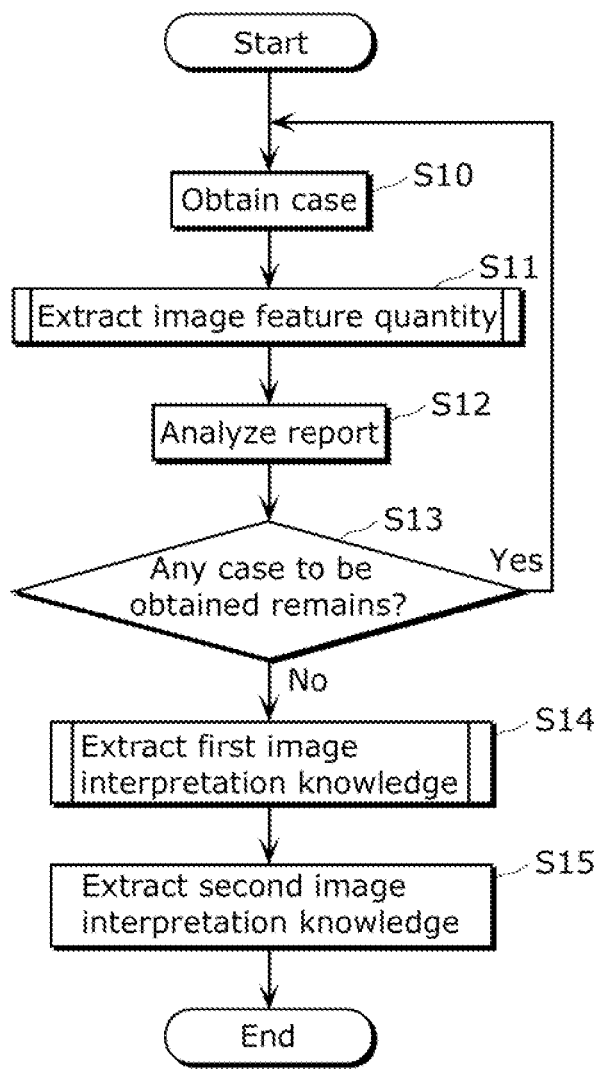
FIG. 2 is a flowchart of a procedure for generating image interpretation knowledge according to Embodiment 1.
Figure 3:
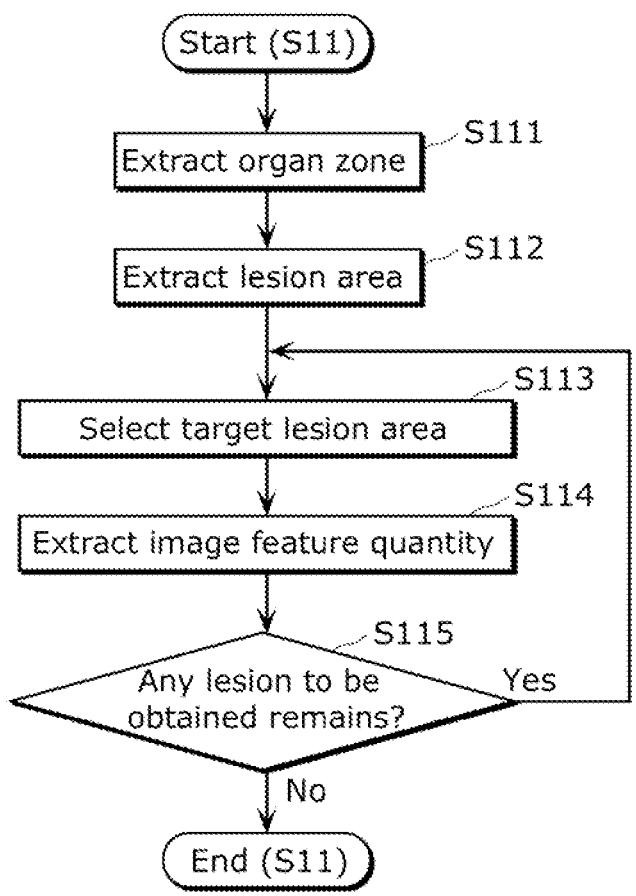
FIG. 3 is a flowchart of a procedure for extracting image feature quantities according to Embodiment 1.

In Step S12 in FIG. 2, a process for analyzing an image interpretation report is performed. More specifically, the image interpretation items and the disease name are extracted from the image interpretation report. In this embodiment, a morpheme analysis and a syntax analysis are made using an image interpretation item word dictionary in which image interpretation items are stored and a disease name word dictionary in which disease names are stored. Through these processes, words matching the words stored in the respective word dictionaries are extracted. Examples of morpheme analysis techniques include Non-patent Literatures 5 and 6: MeCab (http://mecab.sourceforge.net) and ChaSen (http://chasen-legacy.sourceforge.jp), and examples of syntax analysis techniques include Non-patent Literatures 7 and 8: KNP (http://nlp.Kuee.kyoto-u.Ac.jp/nl-resource/knp.html), CaboCha (http://chasen.org/~taku/software/cabocha/). Image interpretation reports are often written by doctors using expressions unique to image interpretation reports. Thus, it is desirable to develop morpheme analysis techniques, syntax analysis techniques, and various words dictionaries exclusive for image interpretation reports.

FIG. 4 is an example of an image interpretation report of an abdominal CT scan. FIG. 5 shows image interpretation items and a disease name extracted from the image interpretation report in FIG. 4. Several image interpretation items are normally extracted, while one disease name is extracted. Assuming that the number of image interpretation items extracted from the image interpretation report in the i-the case is $N_i$, each of the image interpretation items can be identified as a pair $(i, j)$ where i denotes the case number, and j denotes the image interpretation item number. Here, $1 \leq i \leq C$ and $1 \leq j \leq N_i$ are satisfied.

In addition, although only the words related to the image interpretation items and disease name are extracted in FIG. 5, it is also possible to extract character strings indicating the positions of lesions in the image interpretation report and character strings indicating time phase at the same time. Here, supplemental information regarding the time phases is provided. It is considered that a contrast radiography for time-series image capturing using a rapid intravenous injection is useful for identifying a lesion in a liver. In a contrast radiography of a liver, images of the liver are generally captured in the following time phases: an arterial phase in which a contrast medium is infused into a liver artery and a stain of a polycythemia tumor is observed; a portal venous phase in which the contrast medium distributed in a intestinal tract and a spleen is infused from a portal vein to the liver, and a hepatocyte has a highest contrast; an equilibrium phase in which the contrast medium inside and outside the blood vessels of the liver reaches its equilibrium; and a late phase in which the contrast medium stays in a stroma of the liver. Image interpretation reports often include descriptions of information about the positions of lesions in organs, and information about time phases focused in contrast radiography. For this reason, the information about the positions and the information about time phases extracted together with the image interpretation items are effective for the extraction of necessary information from the image interpretation knowledge described later. FIG. 6 shows an example where the information about the positions and the information about time phases are extracted together with the image interpretation items. For example, in the case of an analysis of an image interpretation report in FIG. 4, from a sentence clause that "Early stain is observed in liver segment S3", the "Liver segment S3" is extracted as a position attribute of the "Early stain". Likewise, from a sentence clause that "Washout is observed in late phase", the "Late phase" is extracted as a time phase attribute of "Washout".

When the image interpretation report in FIG. 4 is simply interpreted, the column for the time phase related to the "Early stain" and the column for the position related to the "Washout" are blanks in the table of FIG. 6. On the other hand, when it is possible to utilize prepared knowledge that the image interpretation item "Early stain" is a term related to the early phase and to perform a context analysis that the tumor indicating the state of the "Early stain" refers to the tumor that is washed out in the "Late phase", the information about the position and the information about the time phase extracted in this case are as shown in FIG. 7.

In Step S13, a check is made to detect whether or not any case to be obtained remains in the database storing cases for obtaining information from image interpretation knowledge. When a case to be obtained remains, a return is made to Step S10, the un-obtained case is obtained, and Steps S11 and S12 are executed. When no a case to be obtained remains, in other words, an image feature extraction in Step S11 and a report analysis in Step S12 are already completed for each of all the cases, a transition to Step S14 is made.

The results obtained through Step S11 and Step S12 are independent of each other, and thus the execution order may be reversed.

At the time point at which Step S14 is reached, for example, a set of data items shown in FIG. 8 is obtained. In other words, the image feature quantities, the image interpretation items, and the disease name are obtained for each of cases. The case assigned with the case number 1 includes an M1 number of lesions in one or more medical images, and the number of image feature quantities to be extracted from each of the lesions is denoted as NIF. Furthermore, the number of image interpretation items in the image interpretation report is denoted as N1. For example, in the first lesion shown as a lesion number 1 in a set of numbers $(1, 1)$, the value of the first image feature quantity is 0.851. In addition, the value of the first image interpretation item shown as an image interpretation item number 1 in the set of numbers $(1, 1)$ shows "Early stain". In the example of FIG. 8, each of the image feature quantities is any numerical value within a range from 0 to 1 inclusive, and each of the image interpretation items and the disease name is a character string. It is also good to use a negative value or a value larger than 1 as an image feature quantity. Furthermore, it is also good to store each of the image interpretation items and the disease name as a data item in the form of a predefined word ID.

In Step S14, the first image interpretation knowledge is extracted from the image feature quantities obtained in Step S11 and the image interpretation items obtained in Step S12. The process in Step S14 is described in detail with reference to the flowchart in FIG. 9.

In Step S141, one image interpretation item is selected from all the data items described in the table of FIG. 8. These data items are already obtained prior to Step S141. As a selection order, it is possible to use, for example, an entry order (the order of image interpretation item numbers) in an image interpretation item word dictionary used in Step S12. In this embodiment, the number of all entries of image interpretation items in the image interpretation item word dictionary is assumed to be NII. Here, the appearance order of all the data items described in the table of FIG. 8 or an arbitrary order is also possible as the selection order.

In Step S142, a case including the image interpretation item selected in Step S141 in the image interpretation report is selected from among all the data items described in the table of FIG. 8. All kinds (an NIF number) of image feature quantities are obtained from all the lesions included in a medical image of the selected case, and the obtained image feature quantities are stored in a storage area corresponding to the image interpretation item that is currently being selected.

Here, it is highly likely that one case includes a plurality of lesions (tumors) and for which a plurality of images are captured. The image interpretation report of the case includes descriptions about the lesions. For example, in a contrast CT scan, CT images are captured at plural time points (that are plural time phases) before and after the application of a contrast medium. For this reason, sets of slice images are obtained, each of the sets of slice images includes plural lesions (tumors), and a plurality of image feature quantities are extracted from each of the lesions. For this reason, a certain number of image feature quantity vectors having dimensions are obtained. The number of image feature quantities is obtained according to the Expression (the number of sets of slice images, that is, the number of image capturing time phases)×(the number of lesions detected from a patient), and the dimensions corresponds to (the number of kinds of image feature quantities). In addition, it is necessary to calculate the correlations between (i) these image feature quantity vectors and (ii) the disease name and the image interpretation items extracted from the image interpretation report. There is a possibility that such correlations are calculated accurately by using a large number of cases. However, it is possible to calculate the correlations more accurately by associating, in advance, the descriptions in the image interpretation report and the image feature quantities corresponding to the descriptions to some extent as described later. When a case includes plural lesions and one of the lesions and an image interpretation item that is currently being selected is already associated with each other, it is only necessary to store the image feature quantity extracted from only the lesion corresponding to the current image interpretation item.

Figure 10:
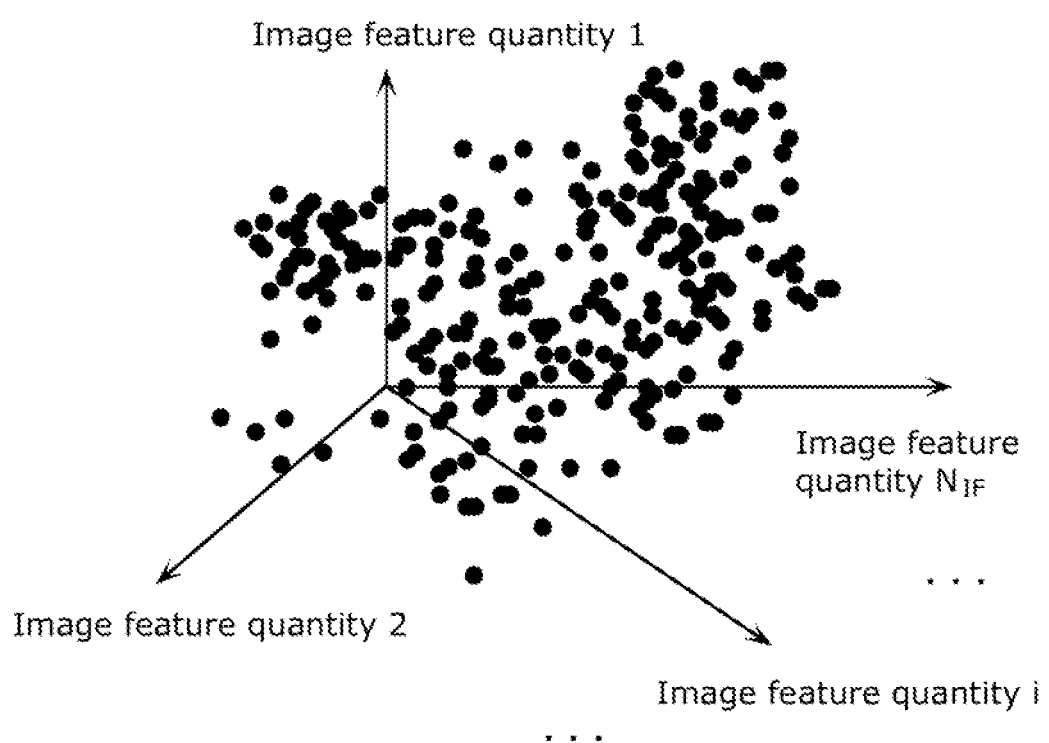
FIG. 10 is a distribution chart that shows a distribution of image feature quantity vectors that corresponds to a given image interpretation item and is the first image interpretation knowledge according to Embodiment 1.

FIG. 10 is a distribution chart schematically showing a distribution of image feature quantity vectors that corresponds to the current image interpretation item and stored in Step S142. In the chart, the image feature quantity vectors are plotted in an NIF-dimensional feature quantity space. Each of the plots in this space corresponds to one of the NIF-dimensional image feature quantity vectors obtained from one of lesion images (that is a partial image extracted from the original slice image such that the partial image includes the lesion area originally included therein).

Figure 9:
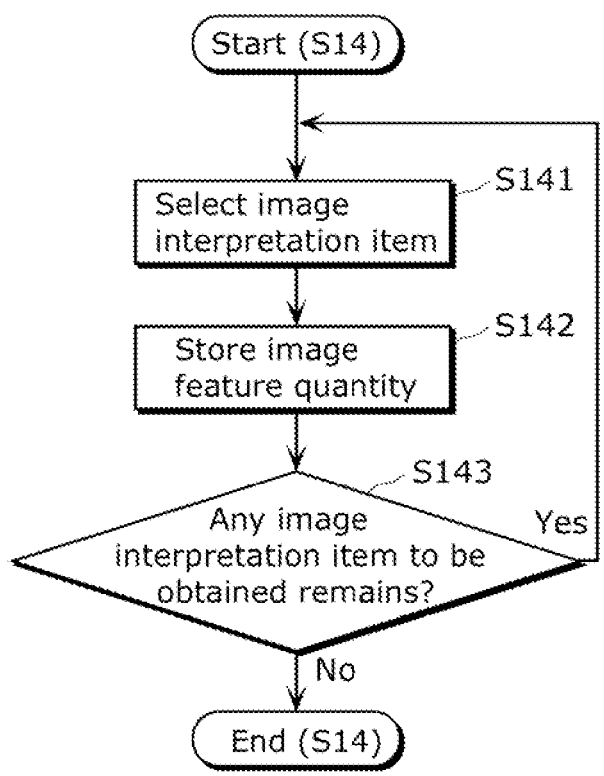
FIG. 9 is a flowchart of a procedure for generating first image interpretation knowledge according to Embodiment 1.

In Step S143, a check is made to find whether or not any image interpretation item to be obtained remains. If any, a return to Step S141 is made. Otherwise, the flowchart of FIG. 9 is terminated.

At this time point, a certain number of distributions of image feature quantity vectors corresponding to a given image interpretation item as shown in FIG. 10 is obtained. The certain number corresponds to the number of image interpretation items. In this embodiment, a distribution as in FIG. 10 is obtained for each of all the entries (NII pieces) in the image interpretation item word dictionary. Each of these distributions is assumed to be included in the first image interpretation knowledge. Each of the obtained distribution, that is, information about the presence range of the values of image feature quantities is stored in the first image interpretation knowledge database 110 in the format as shown in FIG. 11.

FIG. 11 is a table (a storage format) of image feature quantity vectors extracted from an NFi number of lesion images (partial images extracted from the original slice image such that the partial images include the lesion area originally included therein) with respect to the i-th image interpretation image among the NII number of image interpretation items. Each of the image feature quantity vectors extracted from a corresponding one of the lesion images is composed of an NIF number of values (NIF dimensions), and the presence range of these values is [0, 1].

The above-described calculation methods and storage formats of the first image interpretation knowledge are the most basic examples. Other examples are described in the later-provided explanations of similar case searches.

Next, in Step S15, second image interpretation knowledge is extracted from the image feature quantities obtained in Step S11 and the image interpretation items and the disease name obtained in Step S12. In this embodiment, two data correlations between image feature quantities and image interpretation items are assumed to be image interpretation knowledge.

Hereinafter, in addition to (i) the correlations between image feature quantities and image interpretation items, descriptions are given of (2) the correlations between image feature quantities and disease names and (3) the correlations between image interpretation items and disease names.

(1) Correlation Between Image Feature Quantity and Image Interpretation Item

A description is given of how to obtain the correlation between an image feature quantity and an image interpretation item in a pair. A correlation ratio is used here from among several kinds of representation forms of correlations. A correlation used here is an index indicating the correlation between a qualitative data item and a quantitative data item, and presented in Expression 1.

[Math. 1]

$$\eta^2 = \frac{\sum_i N_i(\bar{x}_i - \bar{x})^2}{\sum_i \sum_j N_i(x_{ij} - \bar{x})^2} = \frac{S_B}{S_T} \quad \text{(Expression 1)}$$

Here, $x_{ij}$ is an i-th observed value that belongs to category i of the qualitative data.

$\bar{x}_i$ denotes the average value of observed values that belong to the category i of the qualitative data;

$\bar{x}$ denotes the overall average value;

$N_i$ denotes the number of observations that belong to the category i;

$S_B$ denotes an inter-category variance; and $S_T$ denotes a total variance.

Image interpretation reports are classified into two categories based on the presence/absence of a certain image interpretation item, and these categories are assumed to be qualitative data items. The raw values of image feature quantities of a kind extracted from the medical images are assumed to be qualitative data items. For example, for each of the cases included in the case database for extracting image interpretation knowledge, the image interpretation reports are classified into the categories one of which includes image interpretation reports which include the certain image interpretation item and the other includes image interpretation reports which do not include the certain image interpretation item. Here, a description is given of an approach for calculating the correlation ratio between the image interpretation item "Early stain" and the image feature quantity "Average luminance value inside tumor in early phase". In Expression 1, it is assumed that the category i=1 includes the "Early stain", and that the category i=2 does not include the "Early stain". Here, $x_{1j}$ denotes the i-th observed value that is the "Average luminance value inside tumor in early phase" in the tumor image extracted from the case whose image interpretation report(s) include(s) the "Early stain". Here, $x_{2j}$ denotes the j-th observed value that is the "Average luminance value inside tumor in early phase" in the tumor image extracted from the case whose image interpretation report(s) do(es) not include the "Early stain". The "Early stain" indicates that a CT value increases in the early phase in the contrast radiography, and thus the correlation ratio is expected to be increased (to a value close to 1) in this case. Furthermore, the early stain depends on the type of the tumor, but does not depend on the size of the tumor, and thus the correlation between the image interpretation item "Early stain" and an image feature quantity "Tumor size" is small (a value close to 0). In this way, the correlations between all the image interpretation items and all the image feature quantities are calculated.

Figure 12:
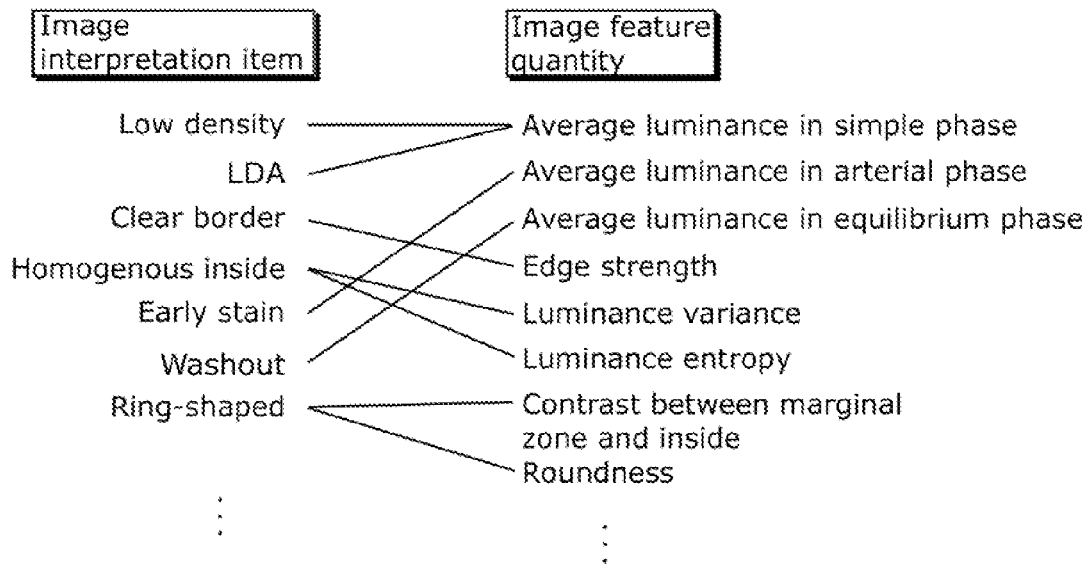
FIG. 12 is a conceptual chart of correlations (in a two-value representation) between image interpretation items and image feature quantities according to Embodiment 1.

FIG. 12 is a conceptual chart of correlations (here, correlation ratios) between image interpretation items and image feature quantities. The image interpretation items are listed at the left side, and the names of the image feature quantities are listed at the right side. Each of pairs of an image interpretation item and an image feature quantity having a correlation value larger than or equal to a threshold value is connected by a solid line. Each of the correlation ratios is any value within a range from 0 to 1 inclusive, and thus any value approximately within a range from 0.3 to 0.7 inclusive can be used as the threshold value. When the calculated correlation ratios are finally binarized based on the threshold value, information as shown in FIG. 12 is obtained. Supplemental information is given for this example. In contrast CT scans for detecting liver tumors, most tumors are drawn in a low density in CT images (that are called as simple images, simple CT images, simple phases, or the like) obtained before the application of contrast media are used. In most cases, the image interpretation reports of the tumors include any one of descriptions of "Low density", "Low Density Area (LDA) observed", or the like. For this reason, high correlations are observed between the image interpretation items such as "Low density" and "LDA" and the average luminance values inside the tumors in the CT images before the application of the contrast media (an example of the average luminance values is shown as an abbreviated version that is "Average luminance in simple phase").

Figure 13:
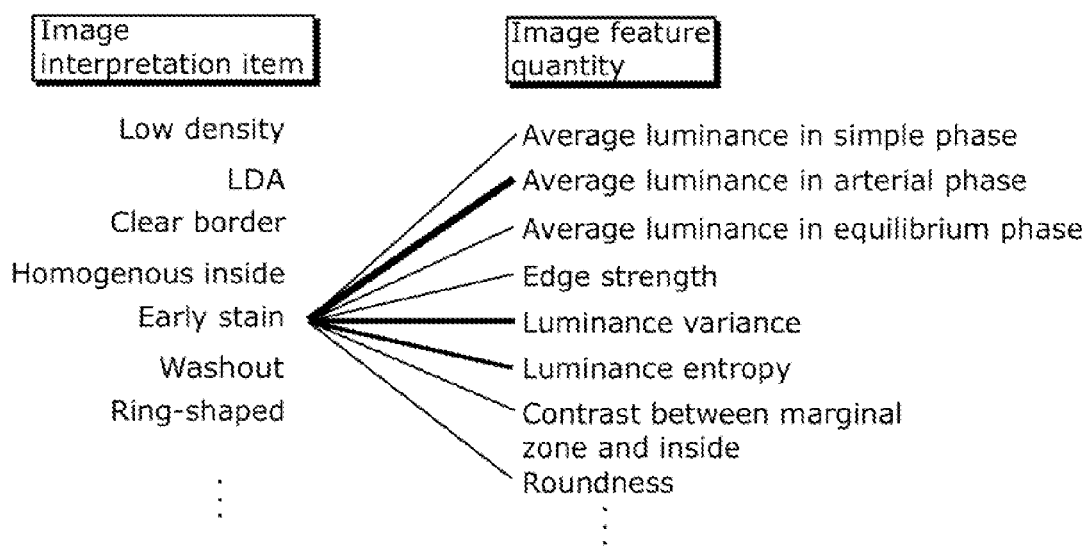
FIG. 13 is a conceptual chart of correlations (in a multi-value representation) between image interpretation items and image feature quantities according to Embodiment 1.

FIG. 13 is a conceptual chart of correlations (here, correlation ratios) between image interpretation items and image feature quantities. In this chart, the correlation ratios between the image interpretation items and the image feature quantities are shown in a multi-value representation in which the boldness of the solid lines corresponds to the magnitudes of the correlation ratios. For example, the highest correlation is observed between the "Early stain" related to the early phase in which the CT value increases in the contrast radiography and the average luminance value inside the tumor (abbreviated as "Average luminance in arterial phase" in FIG. 13) in the early arterial phase (abbreviated as "Early phase" or "Arterial phase").

Focusing on these values of the correlation ratios makes it possible to identify the image feature quantities highly related to the certain image interpretation item. In reality, it is highly likely that one case includes a plurality of lesions (tumors) and for which a plurality of images are captured. The image interpretation report of the case includes descriptions about the lesions. For example, in a contrast CT scan, CT images are captured at plural time points before and after the use of a contrast medium. For this reason, sets of slice images are obtained, each of the sets of slice images includes plural lesions (tumors), and a plurality of image feature quantities are extracted from each of the lesions. For this reason, the number of image feature quantities is obtained according to the Expression (the number of sets of slice images)×(the number of lesions detected from a patient)×(the number of kinds of image feature quantities). In addition, it is necessary to calculate the correlation between (i) each of the image feature quantities and (ii) each of corresponding ones of the image interpretation items and the disease name extracted from the image interpretation report. There is a possibility that such correlations are calculated accurately using a large number of cases. However, it is possible to calculate the correlations more accurately by associating, in advance, the descriptions in the image interpretation reports and the image feature quantities corresponding to the descriptions to some extent based on, for example, the lesion positions and time phases as in FIG. 7.

In the above description, the image interpretation reports are classified into two categories based on the presence/absence of the certain image interpretation item. However, the image interpretation reports are classified into two categories based on the presence/absence of the certain image interpretation item (for example, "Clear border") and the antonym image interpretation item (for example, "Unclear border"). If the image interpretation items are presented in an ordinal scale represented as descriptions "Low density", "Medium density", and "High density", it is possible to calculate the correlation ratios these descriptions as categories (three categories in this example).

Furthermore, the synonyms such as "Low density", "Low luminance", and "Low absorption" are associated with each other as the identical image interpretation item in a synonym dictionary prepared in advance and handled as such.

(2) Correlation Between Image Feature Quantities and Disease Name

Figure 14:
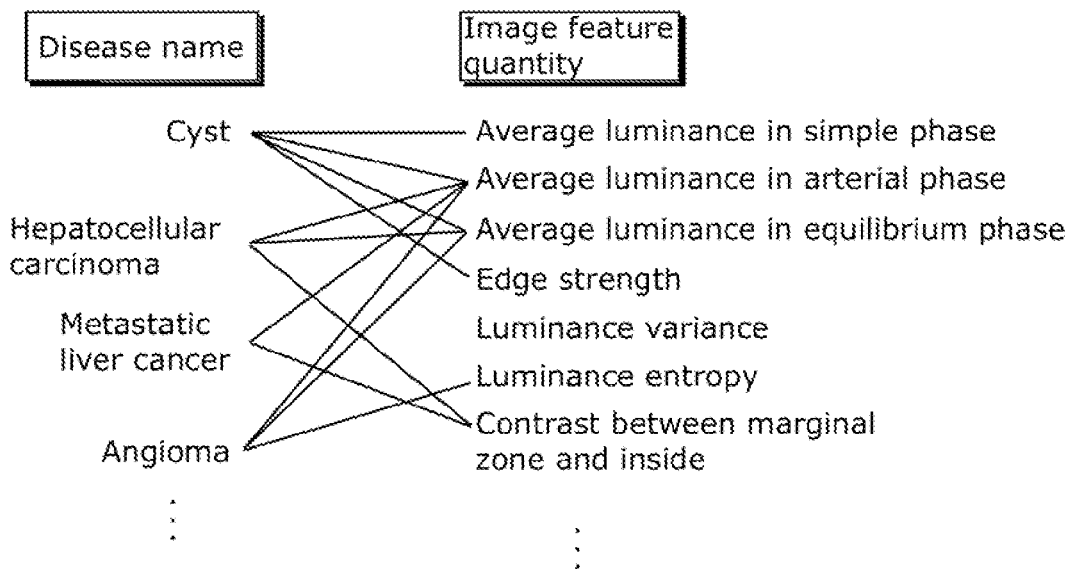
FIG. 14 is a conceptual chart of correlations (in a two-value representation) between disease names and image feature quantities according to Embodiment 1.

Correlation ratios can be used as the correlations between image feature quantities and a disease name in pairs, as in the example of the image feature quantities and image interpretation items in the pairs. FIG. 14 is a conceptual chart of correlations (here, correlation ratios) between the disease names and the image feature quantities. The correlations are shown in a binary representation as in FIG. 12, but it is naturally possible to use a multi-value representation as in FIG. 13.

(3) Correlation Between Image Interpretation Items and Disease Names

A description is given of how to calculate the correlation between an image feature quantity and an image interpretation item in a pair. A log-likelihood ratio is used here from among several kinds of representation forms of correlations. The log-likelihood ratio is an index indicating the strength of co-occurrence between qualitative data items, and is represented according to Expression 2.

[Math. 2]

$$G(X, Y) = a\log\frac{aN}{(a+b)(a+c)} + b\log\frac{bN}{(a+b)(b+d)} + c\log\frac{cN}{(a+c)(c+d)} + d\log\frac{dN}{(b+d)(c+d)}$$ (Expression 2)

Here, X denotes an image interpretation item, and Y denotes a disease name.

Each of a, b, c, and d denotes an appearance frequency of a combination of words.

|  | Y | ¬Y | Sum |
|---|---|---|---|
| X | a | b | a + b |
| ¬X | c | d | c + d |
| Sum | a + c | b + d | N | a denotes the co-occurrence frequency of Words X and Y;
b denotes the appearance frequency of Word X;
c denotes the appearance frequency of Word Y; and
d denotes the no-appearance frequency of Words X and Y.

As clear from Expression 2, the log-likelihood ratios can be regarded as co-occurrence indices defined considering Events X and Y, and Exclusive events ¬ X and ¬ Y.

It is also possible to use, for example, support values shown in Expression 3, confidence values shown in Expression 4, and lift values shown in Expression 5, instead of the log-likelihood ratios. Alternatively, it is also possible to use conviction and phi-coefficients. Conviction values and phi-coefficients are described in documents related to a correlation rule analysis. An example of such documents is Non-patent Literature 9: "Data Mining and its Applications", written by Kato, Hamuro, and Yata, Asakura Publishing Co. Ltd.

[Math. 3]

$$\operatorname{support}(X \Rightarrow Y) = \frac{\operatorname{count}(X \cup Y)}{|D|} \quad \text{(Expression 3)}$$

Here, X, Y are arbitrary item sets (X, Y $\subseteq$ I);

|D| is the number of all transactions; and count (X) is the number of transactions including the item set X in a database D.

Here, a correlation rule between an image interpretation item and a disease name in each pair is calculated. The definitions of the terms are modified as indicated below.

X denotes one image interpretation item;

$I_1$ of X $\subseteq$ $I_1$ denotes the item set related to an image interpretation item;

Y denotes one disease name;

$I_2$ of Y $\subseteq$ $I_2$ denotes the item set related to a disease name;

|D| denotes the number of all transactions; and count (X $\cup$ Y) is the number of cases whose image interpretation reports include both of the image interpretation item X and the disease name Y.

Each of these support values means a probability (co-occurrence probability) of co-occurrence of the interpretation item X and the disease name Y in each of the cases. When the interpretation item X and the disease name Y simultaneously appear in most of the interpretation reports of the cases, the interpretation item X and the disease name Y are regarded as having a high correlation.

[Math. 4]

$$\operatorname{confidence}(X \Rightarrow Y) = \frac{\operatorname{count}(X \cup Y)}{\operatorname{count}(X)} = P(Y|X) \quad \text{(Expression 4)}$$

Here, X, Y are arbitrary item sets (X, Y $\subseteq$ I); and count (X) is the number of transactions including the item set X in a database D.

Each of these confidence values means a probability of the appearance of the conclusion portion Y under the condition that the item of the condition portion X appears. When the disease name Y appears in any of the interpretation reports in which the image interpretation item X appears, the interpretation item X and the disease name Y are regarded as having a high correlation.

[Math. 5]

$$\operatorname{lift}(X \Rightarrow Y) = \frac{\operatorname{confidence}(X \Rightarrow Y)}{P(Y)} = \frac{P(Y|X)}{P(Y)} \quad \text{(Expression 5)}$$

Here, X, Y are an arbitrary set of items (X, Y $\subseteq$ I);

count (X) is the number of transactions including the item set X in a database D;

P (Y) denotes the appearance probability of the item set Y; and $$P(Y) = \frac{\operatorname{count}(Y)}{|D|}$$

|D| denotes the number of all transactions.

Each of the lift values is an index showing how much the appearance probability (that is the confidence value) of the disease Y increases under the condition that the image interpretation item X appears, with respect to the appearance probability of the disease name Y without the condition that the image interpretation item X of appears. When the lift value is 1.0, the appearance probability of the disease name Y does not change even when the image interpretation item X does not appear, and thus the rule is of interest (this rule is "the image interpretation item X $\Rightarrow$ the disease name Y" which means that the disease name is Y when the image interpretation item is X). This means that the appearance of the image interpretation item X and the appearance of the disease name Y are statistically independent of each other. The rule is regarded as being of higher interest as the lift value is more higher than 1.0. In other words, the correlation between the image interpretation item X and the disease name Y is regarded as being higher.

Figure 15:
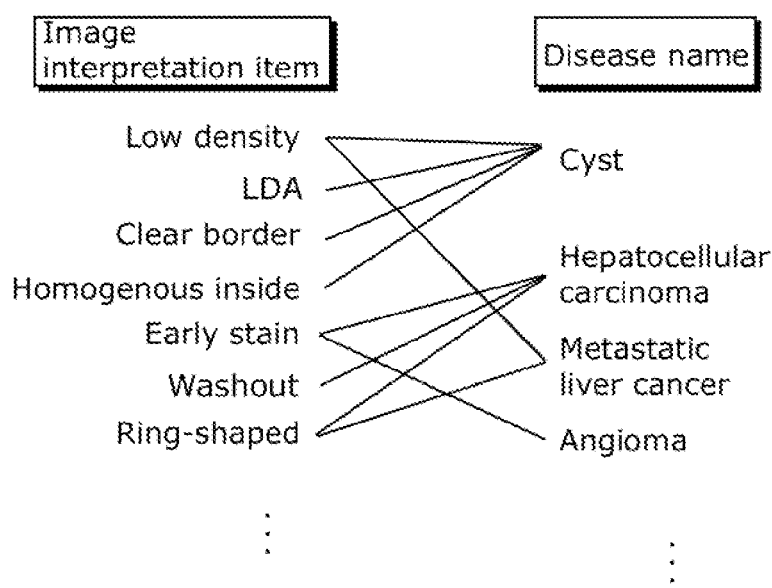
FIG. 15 is a conceptual chart of correlations (in a two-value representation) between image interpretation items and disease names according to Embodiment 1.

FIG. 15 shows a conceptual chart of correlations (for example, log-likelihood ratios) between image interpretation items and disease names. The correlations are shown in a binary representation as in FIG. 12, but it is naturally possible to use a multi-value representation as in FIG. 13.

When performing Step S15 according to the aforementioned approach, the following are respectively obtained: the correlations between image feature quantities and image interpretation items as in FIG. 16; the correlations between image feature quantities and disease names as in FIG. 17; and the correlations between image interpretation items and disease names as in FIG. 18. The numerical values in the table are correlation ratios in FIG. 16 and FIG. 17, and are log-likelihood ratios in FIG. 18. The log-likelihood ratios are any values larger than or equal to 0. In addition, the obtained correlations are stored in the second image interpretation knowledge database 120 in the forms of FIG. 16, FIG. 17, and FIG. 18.

(Similar Case Search)

Hereinafter, a description is given of a procedure of a search for a similar case using a flowchart in FIG. 19 and an example of an image screen for a similar case search in FIG. 20.

Figure 20:
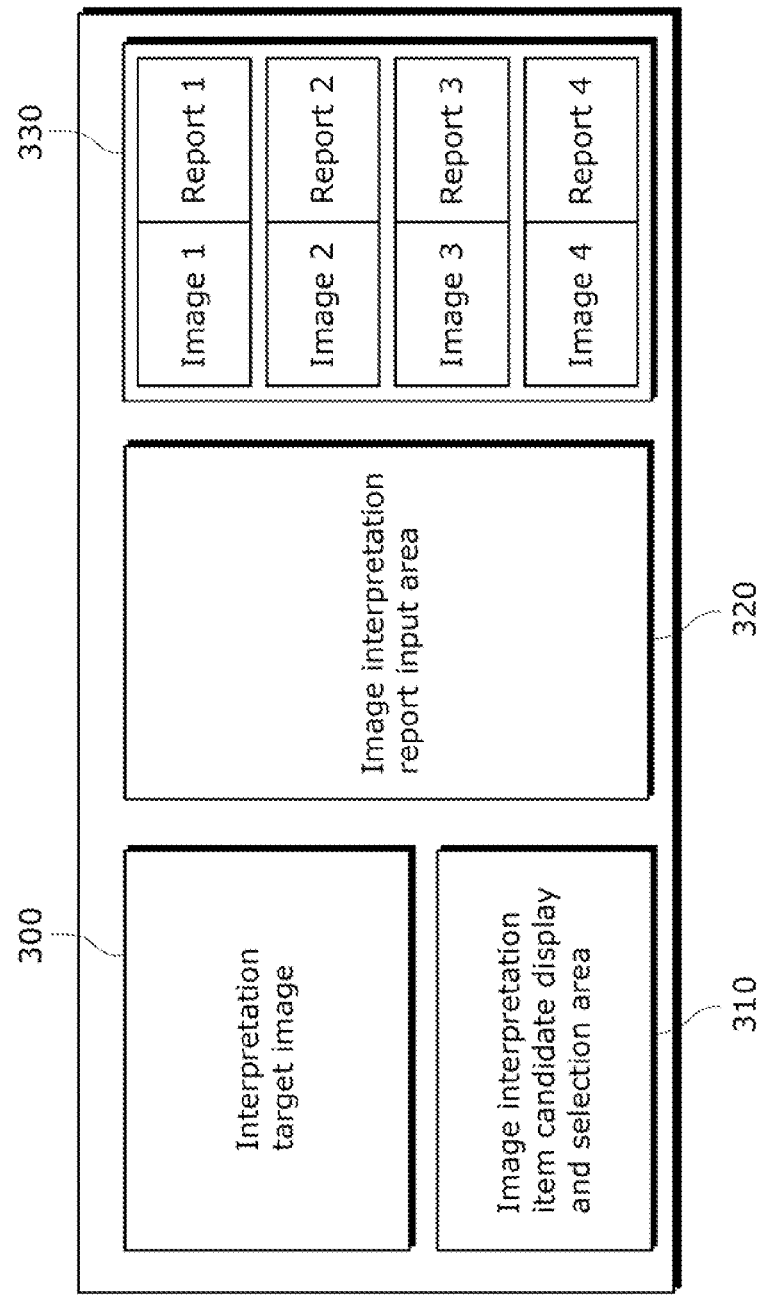
FIG. 20 is an illustration of an example of a similar case searching display screen according to Embodiment 1.

The exemplary similar case search display screen shown in FIG. 20 is of the image interpreting terminal 220 comprising: the interpretation target image display unit 140, the image interpretation item candidate display unit 170, the image interpretation item selecting unit 180, the similar case display unit 210 which are all shown in FIG. 1; and the image interpretation report input unit (not shown in FIG. 1).

In Step S30, the interpretation target image reading unit 130 obtains the interpretation target image from the medical image capturing apparatus. As in the generation of image interpretation knowledge in FIG. 2, the medical image capturing apparatus that is the target in this embodiment is a multi-slice CT apparatus, and the target organ and disease is a liver tumor. The read image (the target image 300 in FIG. 20) is displayed on the interpretation target image display unit 140.

In Step S31, a user specification of a target lesion for which a similar case search is requested is received. This specification is made by clicking a lesion part using a mouse on a display screen (an interpretation target image 300) of the interpretation target image display unit 140.

How to specify this lesion is described. As the specification scheme, it is possible to specify one point around the center of the lesion, or to specify the lesion area (or the outline of the lesion area). When the one point around the center is specified, a detailed lesion area is set using the same scheme as in Step S112 from a proximity area with respect to the specified point. When the lesion area is roughly specified, the detailed lesion area is specified in the roughly-specified lesion area using the same scheme as in Step S112.

Figure 21:
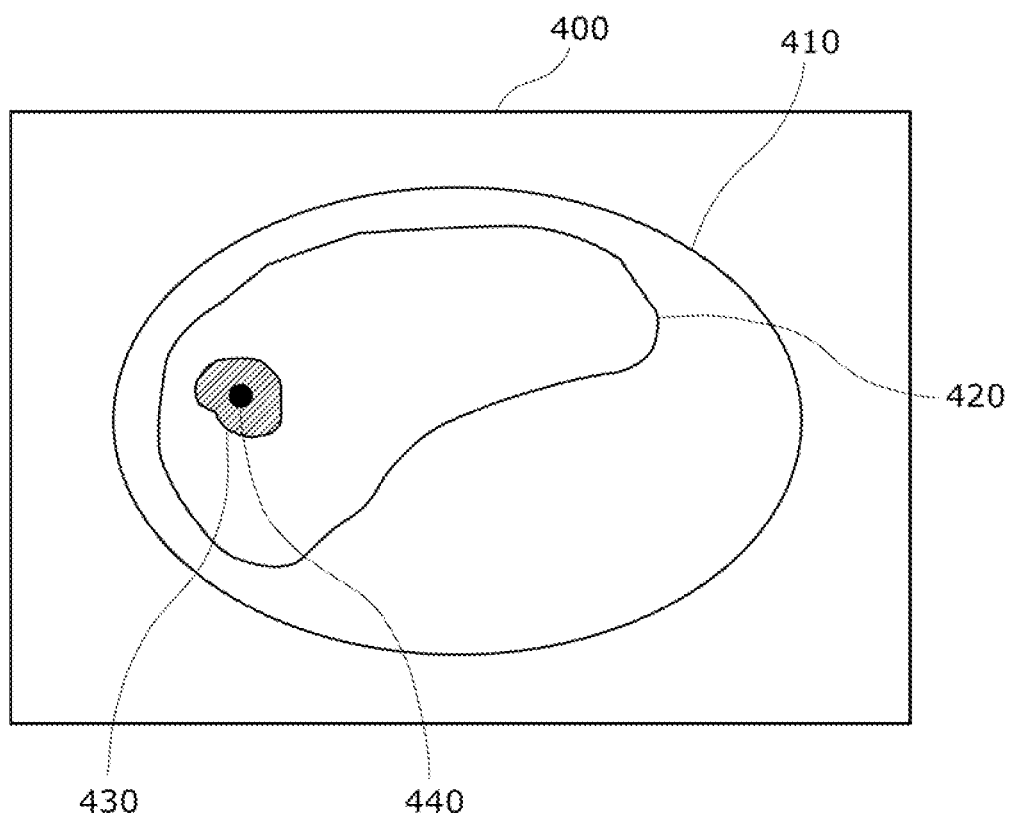
FIG. 21 is an illustration of a specification of a lesion position or a lesion area according to Embodiment 1.

FIG. 21 illustrates a specification of the lesion position or the lesion area. An interpretation target image 400 (an abdominal CT image here) shown in FIG. 21 includes an abdominal part 410, a target organ (a liver here) 420, and a lesion area 430. When a coordinate is specified, for example, an approximately center position (a point 440 in FIG. 21) of a tumor is clicked using a mouse. Examples of schemes to specify an area include, a scheme for enclosing the lesion area 430 in FIG. 21 by a rectangle, a circle, or an oval circle, and a scheme for specifying a boundary between the lesion portion (the lesion area 430 in FIG. 21) and a normal organization (the outside of the lesion area 430) using a free-form curve. The scheme for specifying only the center coordinate or specifying the area by enclosing the area by the rectangle, the circle, or the over circle has an advantage of placing a small burden on the user, but requires that the accurate lesion area is automatically extracted using an image processing algorithm for an image feature quantity extraction. As for a tumor area extraction, the same approach as in Step S112 can be used.

In Step S32, the image feature quantity extracting unit 150 extracts image feature quantities from each of the lesion areas specified or extracted in the interpretation target image in Step S31. When plural lesion areas are specified or extracted, a predefined NIF number of feature quantities are extracted for each of the lesion areas. The scheme for extracting the image feature quantities is the same as in Step S114.

In Step S33, the image interpretation item fitting degree calculating unit 160 calculates a fitting degree with respect to each of all the (NII number of) image interpretation items, using the image feature quantities extracted in Step S32. Here, the concept of fitting degree calculation is described. FIG. 10 is a distribution of image feature quantity vectors extracted from cases including a given image interpretation item in the image interpretation reports of the cases. The image feature quantities extracted are plotted in the space of FIG. 10. When many image feature quantities extracted from previous cases are present around the extracted image feature quantities, it is highly likely that the given image interpretation item fits the current interpretation target image. Here, image feature quantities (vector elements) having a small correlation with the given image interpretation item should not be considered. Thus, the image interpretation item fitting degree calculating unit 160 selects image feature quantities (vector elements) having a high correlation with the given image interpretation item, based on the correlations between image feature quantities and image interpretation items in the second image interpretation knowledge database, and uses the selected image feature quantities.

For example, a fitting degree is calculated using an inverse according to Expression 6.

[Math. 6]

$$D_W(x, u^i) = \sqrt{\sum_{j=1}^{n} w_j(x_j - u^i_j)^2}$$ (Expression 6)

x denotes an unknown vector;
$u^i$ denotes the i-th vector among comparison targets;
n denotes the number of dimensions of a vector; and
$w_j$ denotes the weight to the j-th dimension.

Here, x denotes a vector to which all the (NIF number of) image feature quantities extracted from the interpretation target image are connected. When connecting different kinds of image feature quantities, canonicalization (the normalization to the average 0 and the disperse 1) is performed in advance so as not to affect the difference in the scales of the feature quantities. Here, u' denotes an average vector in the distribution of image feature quantities with respect to a current target image interpretation item i. This average value may be replaced with a median value. As a weight $w_j$, the correlation between the image interpretation item i and the image feature quantity j is used. This correlation can be obtained with reference to the value in the corresponding cell of the table stored in the second image interpretation knowledge database 120 in the form of the table of FIG. 16. Using the correlation between the image interpretation item i and the image feature quantity j as the weight wj reduces the influence of an image feature quantity in a given dimension to a fitting degree more significantly as the correlation is smaller. Thus, the use of the correlation makes it possible to calculate the fitting degree with the reduced influence of the image feature quantity in the given dimension having a small correlation with the image interpretation item i.

Alternatively, a binarized value of the correlation between the image interpretation item i and the image feature quantity j may be used as the weight wj. As a specific example, it is assumed that the weight wj is 1 when the correlation is greater than or equal to a predetermined threshold value, and otherwise, the weight wj is 0. When using the binarized correlation as the weight wj, unnecessary dimensions of each of the image feature quantities is determined according to the image interpretation item. When the second image interpretation knowledge is already calculated before the first image interpretation knowledge is calculated, it is possible to reduce the amount of data stored in the first image interpretation knowledge by excluding image feature quantities in the unnecessary dimensions (the shaded parts in the table of FIG. 22) from the table and storing the table without the unnecessary data. As mentioned above, the image feature quantities in the unnecessary dimensions are hatched in FIG. 22.

In the above description, the average value (or the median value) is used as the representative value ui in the distribution of each of the dimensions of the image feature quantity according to FIG. 6. However, when the image feature quantity has a multi-peak distribution instead of a single-peak distribution, it is impossible to sufficiently present the original distribution of the image feature quantity according to Expression 6. In this case, for example, it is also good to present the distribution using, for example, the Gaussian Mixture Model (GMM) according to Expression 7. Here, x denotes a variable in N dimensions (N≥1), M denotes the number of mixture, μm denotes the average of the m-th normal distribution, Σn denotes a variance-covariance matrix of the m-th normal distribution, and λm denotes the mixture ratio (1≤m≤M).

[Math. 7]

$$p(x) = \sum_{m=1}^{M} \lambda_m N\left(x; \mu_m, \sum_m\right)$$ (Expression 7)

In addition, as for the calculation (modeling) of GMM distribution parameters, it is possible to use an Expectation Maximization (EM) algorithm. The data used as an input in the distribution modeling is data from which unnecessary dimensions (the hatched parts in the table) in FIG. 22 are already excluded. The reason why such input data is used is because the values of image feature quantities having a small correlation with a given image interpretation item are distributed in a wide range, and thus the convergence in the GMM distribution parameter calculation is delayed, or the modeling error is increased.

When the GMM parameters are calculated for the respective dimensions of the image feature quantity, the calculated parameters are stored as the first image interpretation knowledge in the first image interpretation database 110 in the form of the table of FIG. 23. Here, the numbers of dimensions of image feature quantities varies for each image interpretation item (for example, the number of dimensions for an image interpretation item 1 is NIF1' dimensions, but the number of dimensions for an image interpretation item 2 is NIF2' dimensions. This variation is caused because unnecessary dimensions for each image interpretation item are already excluded as shown in FIG. 22.

When multi-dimensional GMM parameters are calculated, the calculated parameters are stored in the first image interpretation knowledge database 110 in the form of the table of FIG. 24. The parameters in FIG. 24 are, for example, the M, μm, Σm, and λm (1≤m≤M) according to Expression 7. These parameters in FIG. 23 are used according to Expression 7 where x denotes a scalar value, M denotes the number of mixtures, μm denotes the average value in the m-th normal distribution, μm denotes a variance in the m-th normal distribution, and λm denotes the mixture ratio (1≤m≤M).

In FIG. 23 and FIG. 24, the same dim-dimensional variables (p1, p2, . . . pdim) are used as the distribution parameters. However, modeling target distributions vary, and thus the numbers of post-modeling normal distributions also vary. In other words, the values of the total numbers dim of parameters also vary.

Alternatively, it is possible to present the distributions using a non-parametric approach such as the Parzen estimation, instead of a parametric approach such as the EM algorithm.

In the case of GMM, it is possible to substitute, as x, each of (an NIF number) of image feature quantity vectors extracted from an interpretation target image, and use the output likelihood p (x) as a fitting degree.

Here, the image interpretation item fitting degree calculating unit 160 may calculate the fitting degree using all the image feature quantities, without using the correlations between the image feature quantities and image interpretation items in the second image interpretation knowledge database 120. In other words, it is also good to calculate a fitting degree assuming that the weight wj is 1 irrespective of j according to Expression 6.

In Step S34, the image interpretation item candidate display unit 170 displays image interpretation items having a high fitting degree among fitting degrees with respect to an NII number of image interpretation items calculated in Step S33. More specifically, the image interpretation item candidate display unit 170 displays image interpretation items having a high fitting degree on its display screen (an image interpretation item candidate display and selection area 310 in FIG. 20) in the form of the table of FIG. 25. In FIG. 25, among the NII number of image interpretation items, the image interpretation items having the high fitting degree with respect to a current interpretation target image are displayed in the descending order of their fitting degrees. A predetermined number of image interpretation items may be displayed, or image interpretation items having a fitting degree greater than or equal to a threshold value may be displayed. Alternatively, the user may set the number of image interpretation items to be displayed. When there are plural images of an organ or a lesion in a contrast radiography or the like, it is also good to display, for each image, image interpretation items having a high fitting degree as in FIG. 26. Here, the display order may be at random, instead of the descending order of their fitting degrees.

The number of image interpretation items increases as the number of organs or diseases as the targets in the processing by the similar case searching apparatus increases. Therefore, it is unrealistic to cause a user to select image interpretation items from among all the image interpretation items. Estimating image interpretation items based on image feature quantities extracted from an interpretation target image in this way and displaying these image interpretation items in the descending order of their fitting degrees allows the user to easily determine the target image interpretation items.

As shown in FIG. 27, it is also good to display the values of the fitting degrees together with the image interpretation items having a high fitting degree. Displaying the values of the fitting degrees at the same time provides supplemental information for helping the user to select and determine the target image interpretation items (for example, in FIG. 27, the fitting degree of the image interpretation item "Ring-shaped" is smaller than the other three image interpretation items.

Here, the values of the fitting degrees simply presented using numerical values may be displayed in a distinguishable manner, for example, by using different colors or luminances for the characters or the backgrounds thereof. In addition, the values of the fitting degrees may be displayed, for example, in the form of the bar graph as shown in FIG. 28.

In Step S35, a user input of a selection selected from among the image interpretation item candidates displayed in Step S34 is received via the image interpretation item selecting unit 180. The user input is received so that the image interpretation item selected by the user is used as a similarity measurement (viewpoint) in a similar case search. These image interpretation items are displayed in the image interpretation item candidate display and selection area 310 on the display screen in the form of the table of FIG. 25. The user selects and inputs the target image interpretation item on the display screen by clicking the character string indicating the target image interpretation item using the mouse. FIG. 29 shows an example of the selected image interpretation item. In FIG. 29, the selected image interpretation item "Early stain" is highlighted. Here, the user may select the image interpretation item using a keyboard such as a direction key or an Enter key, instead of clicking a Graphical User Interface (GUI, a virtual bottom) on the display screen.

In Step S36, the weight determining unit 190 determines the weight that is used to perform a search with weights based on image feature quantities, using the image interpretation item selected in Step S35.

A specific example of a weighting scheme is described below.

At present, it is assumed that the image interpretation item selecting unit 180 selects "Early stain" and "Washout" as image interpretation items. The weight determining unit 190 obtains the correlations between "Early stain" and all the respective image feature quantities and the correlations between "Washout" and all the respective image feature quantities, with reference to the correlation table between the image feature quantities and the image interpretation items stored in the form of the table of FIG. 16 in the first image interpretation knowledge database 110. Here, the raw numerical values (correlations) indicating the obtained correlations are used as weights, and are respectively denoted as wa, i, wb, and i. Here, i is a subscript showing the type of the image feature quantity. The weight determining unit 190 calculates the weight Wi corresponding to the i-th image feature quantity using these weights according to Expression 8.

[Math. 8]

$$W_i = W_{a,i} + W_{b,i} \quad \text{(Expression 8)}$$

Figure 30:
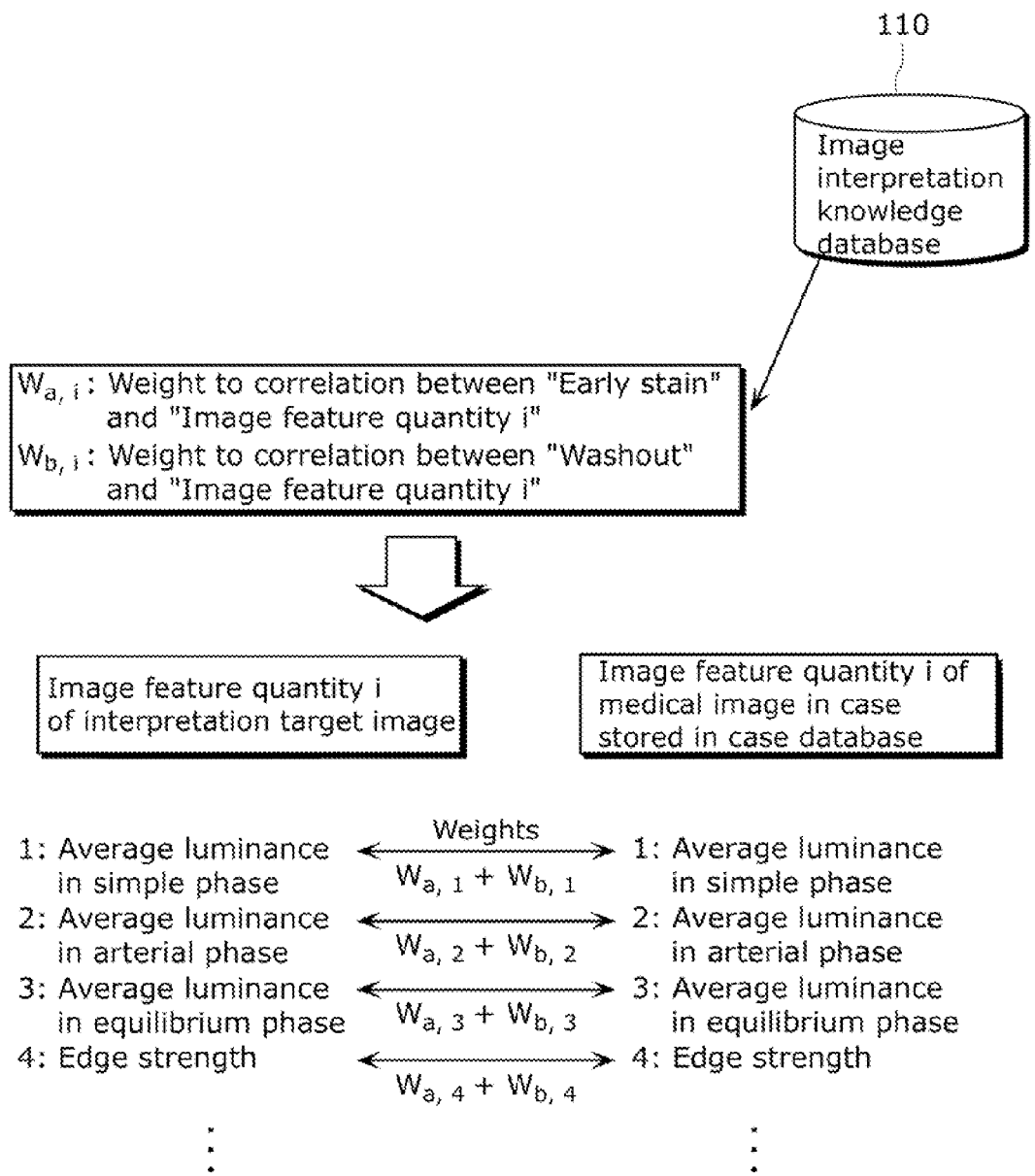
FIG. 30 is an illustration of a weighting scheme in a search for a similar case according to Embodiment 1.

FIG. 30 shows the outline of the weighting scheme described above.

For example, the weight on the fourth image feature quantity "Edge strength" is a value obtained by adding the value wa, 4 indicating the correlation between the early stain and the edge strength and the value wb, 4 indicating the correlation between the washout and the edge strength. When the number of the image interpretation items is other than 2, it is possible to calculate such a value by adding the correlation between the image interpretation item and the image feature quantity. According to this Expression, it is possible to calcuate weights considering image interpretation items on which the doctor is focused, and the correlations between the image interpretation items and the image feature quantities at the same time. As a result, it is possible to perform a similar case search based heavily on these correlations. However, when plural image interpretation items are extracted, these image interpretation items are handled evenly without being differentiated from one another. Additionally using, as a weight, the fitting degree of the selected image interpretation item selected by the user makes it possible to differentiate the respective image interpretation items from one another. For example, in Expression 9, it is possible to weight image feature quantities by using, as wx, the fitting degrees of the respective image interpretation items with respect to the image interpretation item "Early stain" and using, as wy, the fitting degree of the same with respect to the image interpretation item "Washout".

[Math. 9]

$$W_i = W_x W_{a,i} + W_y W_{b,i} \quad \text{Expression 9}$$

Alternatively, it is possible to allow the user to set the weights to the feature quantities with respect to each of selected image interpretation items. For example, FIG. 31 is an exemplary display screen on which the user sets such weights using slide bars. These slide bars are displayed at the right sides of the selected "Early stain" and "Washout". The user changes the weights by sliding leftward or rightward the knobs of the slide bars using the mouse.

In Step S37, the similar case search unit 200 searches the case database 100 for a similar case, using the image feature quantities extracted in Step S32 and the weights determined in Step S36. The searched-out similar case is displayed (in the similar case display area 330 on the display screen) by the similar case display unit 210.

The similar case search unit 200 calculates the weighted distance between each of the image feature quantities extracted from an interpretation target image and a corresponding one of the image feature quantities extracted from a medical image included in a case stored in the case database 100. The similar case search unit 200 searches the case database 100 for similar cases having a weighted distance smaller than a predetermined threshold value. The similar case search unit 200 searches the case database 100 for a predetermined number of similar cases having a small weighted distance selected in the ascending order of their weighted distances.

Each of the weighted distances can be calculated, for example, according to Expression 6. Here, x denotes a vector to which all the (NIF number of) image feature quantities extracted from the interpretation target image are connected. In addition, ui denotes an image feature quantity extracted from the i-th case among the cases stored in the case database 100. When connecting different kinds of image feature quantities, canonicalization (the normalization to average 0 and disperse 1) is performed in advance so as not to affect the difference in the scales of the feature quantities.

In this embodiment, the weighted distance calculation is performed in the similar case search, based on the image interpretation item selected by the user. In other words, the weight to the image feature quantity having a high correlation with the selected image interpretation item is set to be comparatively large, and the weight to the image feature quantity having a low correlation with the selected image interpretation item is set to be comparatively small. In this way, it is possible to perform a similar case search in which the user's focus points are reflected.

In Step S38, the user inputs the image interpretation report via the image interpretation input area 320. In the case of the multi-slice CT apparatus, a plurality of slice images along a vertical surface (the axial view) with respect to the body axis is normally obtained through reconfiguration of the images. The user checks whether or not a lesion (a liver tumor in this embodiment) is present or absent while changing the slice positions on these slice images, and input descriptions in the interpretation report. When inputting descriptions in the interpretation report, the position (the slice number and the coordinate on the slice image or area information) of the lesion detected in the interpretation target image may be specified by the user using an input device such as a mouse. When there is a plurality of lesions in the interpretation target image and a plurality of descriptions is input in the image interpretation report, it is good to clearly record the associations between the lesions in the interpretation target image and the descriptions. Such clear indications of the associations are useful when generating the first image interpretation knowledge database 110 and the second image interpretation knowledge database 120 using the image interpretation report.

Figure 19:
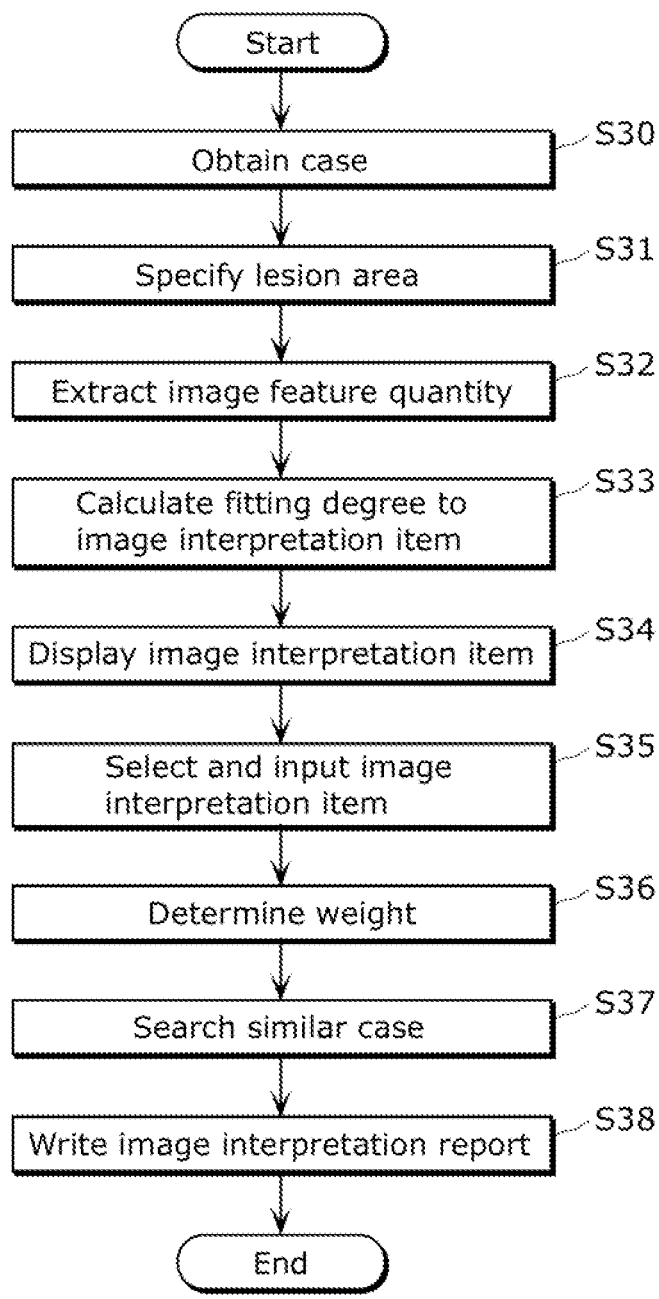
FIG. 19 is a flowchart of a procedure for searching a similar case according to Embodiment 1.

When an image interpretation report input time lasts over a predetermined time or when an input for terminating the image interpretation report input time, the process in FIG. 19 is completed. The processing unit for receiving the similar case search request and the image interpretation termination input is not shown in FIG. 1. The processing unit may be a physical switch embedded in the keyboard or the like in the image interpreting terminal 220, or a GUI menu or the like displayed on the interpretation target image display unit 140 composed of a medical high-definition monitor or the like.

As described above, according to Embodiment 1, image interpretation items are estimated based on image feature quantities extracted from an interpretation target image, and the estimated image interpretation items are displayed for the user in the descending order of their fitting degrees. This enables the user to easily select and determine the target image interpretation item. Using the correlation between an image interpretation item and each of image feature quantities in the calculation of the fitting degree with respect to the image interpretation item reduces the influence of the dimensions of the image feature quantities having a small correlation to the fitting degree. Thus, the use of the correlation makes it possible to calculate the fitting degree with the reduced influence of the image feature quantities having no or little correlation with the image interpretation item. Furthermore, displaying the value of the fitting degree together with the image interpretation item having a high fitting degree provides supplemental information for helping the user to determine the target image interpretation item.

Embodiment 2

Next, Embodiment 2 is described. Unlike Embodiment 1, Embodiment 2 calculates the correlations (co-occurrence correlations) between image interpretation items at the same time when preparing a second image interpretation knowledge database 120. Embodiment 2 is further different from Embodiment 1 in the point of notifying a user of a possible selection error when image interpretation items having a low co-occurrence frequency are selected by the user. These differences from Embodiment 1 are focused in the descriptions given below.

The structure of a similar case searching apparatus according to Embodiment 2 of the present disclosure is basically the same as the structure of a similar case searching apparatus shown in FIG. 1 related to Embodiment 1. The difference from Embodiment 1 is that the image interpretation item candidate display unit 170 according to Embodiment 2 is connected to the second image interpretation knowledge database 120.

(Preparation of Image Interpretation Knowledge Database)

The flowchart of generating an image interpretation knowledge database for a similar case searching apparatus according to Embodiment 2 of the present disclosure is basically the same as the flowchart of FIG. 2 related to Embodiment 1. The operations in Steps S10 to S14 are the same as those in Embodiment 1, and thus the same descriptions are not repeated here.

Next, in Step S15, second image interpretation knowledge is extracted from the image feature quantities obtained in Step S11 and the image interpretation items and the disease name obtained in Step S12. In this embodiment, the image interpretation knowledge assumed to be composed of a combination of (i) two data correlations between image feature quantities and image interpretation items and (ii) two data correlations between image interpretation items. The former is the same as in Embodiment 1, and thus the same description is not repeated here.

Here, the latter that is a generation method is described. The data of FIG. 8 is already obtained at the time of execution of Step S15. Thus, a set of image interpretation items for each of cases is further obtained from the data of FIG. 8. With respect to the obtained set of image interpretation items for each case, the correlations (a log-likelihood ratio of co-occurrence information) between image interpretation items are calculated utilizing the log-likelihood ratio (Expression 2) used to calculate (3) the correlations between the image interpretation items and the disease names obtained in Embodiment 1. The obtained correlations are shown, for example, in the table of FIG. 32. In the table of FIG. 32, since the lower diagonal components are the same as the corresponding upper diagonal components, the diagonal components (the correlations between the same image interpretation items) cannot be calculated and only the upper diagonal components are shown. For example, the log-likelihood ratio between the image interpretation item 1 and the image interpretation item 3 is 0.973, and thus it is highly likely that the image interpretation item 1 and the image interpretation item 3 co-occur.

(Similar Case Search)

The flowchart of a similar case search according to Embodiment 2 of the present disclosure is basically the same as the flowchart of FIG. 19 related to Embodiment 1. The operations in Steps S30 to S34 and Steps S36 to S38 are the same as those in Embodiment 1, and thus the same descriptions are not repeated here.

Figure 33:
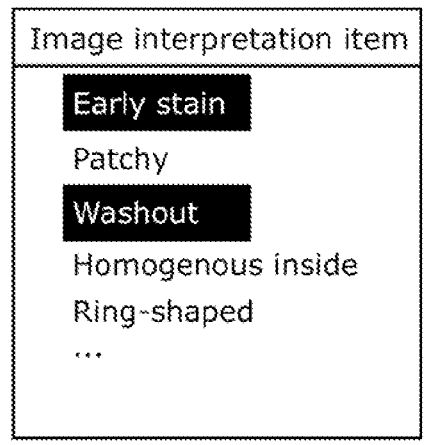
FIG. 33 is a table (a display format) of image interpretation items including image interpretation items selected according to Embodiment 2.

In Step S35, a user input of a selection selected from among the image interpretation item candidates displayed in Step S34 is received via the image interpretation item selecting unit 180. The user input is received so that the image interpretation item selected by the user is used as a similarity measurement (viewpoint) in a similar case search. Image interpretation items having a high fitting degree are displayed on the image interpretation item candidate display and selection area 310 on the display screen, for example, in the form of the table of in FIG. 25. The user selects and inputs the target image interpretation item on the display screen by clicking the character string indicating the target image interpretation item using the mouse. FIG. 33 shows an example of selected image interpretation items. In FIG. 33, one of the selected image interpretation items "Early stain" and "Washout" are highlighted.

Figure 34:
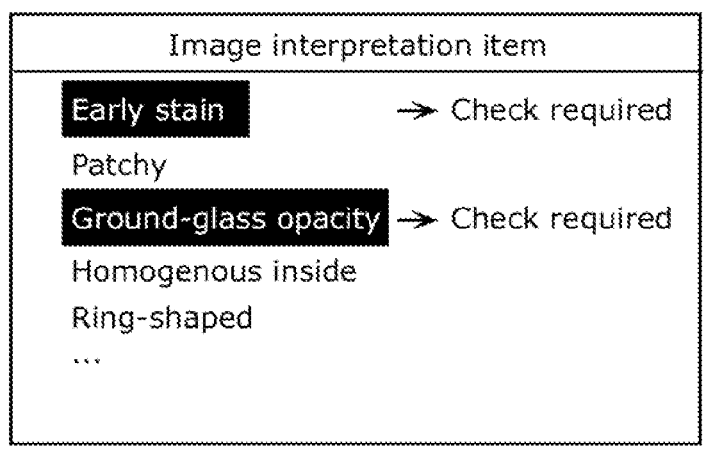
FIG. 34 is a table (a display format) of image interpretation items including selected image interpretation items when displaying a possibility of a selection error with respect to the selected image interpretation item according to Embodiment 2.

Next, when plural image interpretation items are selected, the image interpretation item candidate display unit 170 lists all combinations between the image interpretation items (this process is unnecessary when only one image interpretation item is selected). When an S number of image interpretation items are selected, the number of combinations is denoted as SC2. The image interpretation item candidate display unit 170 obtains the correlations (the log-likelihood ratios of co-occurrence information) for the respective SC2 combinations, with reference to the correlation table of the correlations between the image interpretation items in FIG. 32. When the value of a current one of the obtained correlations is smaller than or equal to a predetermined threshold value, the image interpretation item candidate display unit 170 presents, to the user, a display indicating that the combination of the image interpretation items having the current correlation "may be selected by mistake" because the combination rarely co-occurred in the past. For example, as shown in FIG. 34, a message of "Check required" is assigned to each of the selected image interpretation items (highlighted).

In this way, the user can understand that the combination of the image interpretation items selected by himself/herself with respect to a current interpretation target image is the combination which rarely co-occurred in the past. In this way, the user can determine that the combination may be selected by mistake, and reconsider the selection result utilizing the displayed information.

Embodiment 3

Next, Embodiment 3 is described. Unlike Embodiment 1, Embodiment 3 calculates the correlations (co-occurrence correlations) between image interpretation items at the same time when preparing a second image interpretation knowledge database 120, and makes a setting for disabling a user to select image interpretation items having a low co-occurrence frequency. These differences from Embodiment 1 are focused in the descriptions given below.

The structure of a similar case searching apparatus according to Embodiment 3 of the present disclosure is basically the same as the structure of the similar case searching apparatus in FIG. 1 related to Embodiment 1.

(Preparation of Image Interpretation Knowledge Database)

The flowchart of generating an image interpretation knowledge database for a similar case searching apparatus according to Embodiment 3 of the present disclosure is basically the same as the flowchart in Embodiment 2, and thus the same descriptions are not repeated here. The difference from Embodiment 1 is that the image interpretation item candidate display unit 170 according to Embodiment 2 is connected to the second image interpretation knowledge database 120.

(Similar Case Search)

The flowchart of a similar case search according to Embodiment 3 of the present disclosure is basically the same as the flowchart of FIG. 19 related to Embodiment 1. The operations in Steps S30 to S34 and Steps S36 to S38 are the same as those in Embodiment 1, and thus the same descriptions are not repeated here.

Figure 35:
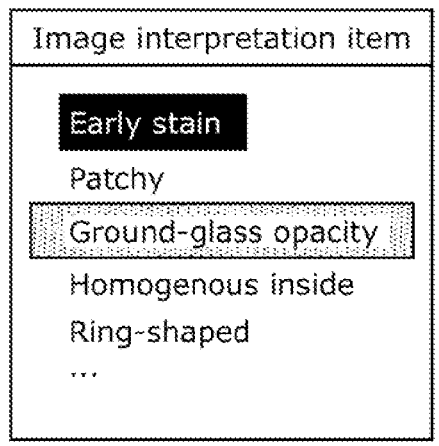
FIG. 35 is a table (a display format) of image interpretation items; the table shows that one of the selected image interpretation items and another one of the selected image interpretation items cannot be selected at the same time according to Embodiment 3 of the present disclosure.

In Step S35, a user input of a selection selected from among the image interpretation item candidates displayed in Step S34 is received via the image interpretation item selecting unit 180. The user input is received so that the image interpretation item(s) selected by the user is used as a similarity measurement (viewpoint) in a similar case search. Image interpretation items having a high fitting degree are displayed on the image interpretation item candidate display and selection area 310 on the display screen, for example, in the form of the table of in FIG. 25. The user selects and inputs the target image interpretation item on the display screen by clicking the character string indicating the target image interpretation item using a mouse. Here, each time a user selects an image interpretation item, the image interpretation item candidate display unit 170 determines an image interpretation items having a correlation value (the log-likelihood ratio of co-occurrence information) with a currently being selected image interpretation item, with reference to a correlation table between image interpretation items in the table of FIG. 32. The image interpretation item candidate display unit 170 makes a display indicating that the determined combination of image interpretation items cannot be selected at the same time. For example, in FIG. 35, it is possible to display the selected image interpretation item "Early stain" in a highlighted manner, and to display the image interpretation item "Ground-glass opacity" in a meshed manner. This shows that the image interpretation item "Ground-glass opacity" cannot be selected when the image interpretation item "Early stain" is selected. Here, the method of displaying such an unselectable image interpretation item may be another method such as a method of reducing the thickness of the characters of the image interpretation item. In addition, it is also possible to display a message such as "Inappropriate combination with image interpretation item "Early stain"" when the user tries to select the image interpretation item "Ground-glass opacity" by clicking the mouse. When the user wishes to prioritize the image interpretation item "Ground-glass opacity" over the other in the selection, it is possible to select the image interpretation item "Ground-glass opacity" by cancelling the selection of the image interpretation item "Early stain".

In this way, the user can recognize a selection error based on previous combinations when selecting an image interpretation item with respect to the current interpretation target image. In this way, it is possible to prevent the occurrence of such a selection error.

Embodiment 4

Next, Embodiment 4 is described. Unlike Embodiment 1, Embodiment 4 calculates the correlations between image interpretation items and disease names at the same time when preparing a second image interpretation knowledge database 120, estimating one of the disease name having a high correlation with a set of image interpretation items currently being selected by the user, and presenting the estimated disease name to the user. These differences from Embodiment 1 are focused in the descriptions given below.

The structure of a similar case searching apparatus according to Embodiment 3 of the present disclosure is basically the same as the structure of the similar case searching apparatus in FIG. 1 related to Embodiment 1. The difference from Embodiment 1 is that the image interpretation item candidate display unit 170 according to Embodiment 2 is connected to the second image interpretation knowledge database 120.

(Preparation of Image Interpretation Knowledge Database)

The flowchart of generating an image interpretation knowledge database for a similar case searching apparatus according to Embodiment 4 of the present disclosure is basically the same as the flowchart of FIG. 2 related to Embodiment 1. The operations in Steps S10 to S14 are the same as those in Embodiment 1, and thus the same descriptions are not repeated here.

Next, in Step S15, second image interpretation knowledge (correlation information in the Claims) is extracted from the image feature quantities obtained in Step S11 and the image interpretation items and the disease name obtained in Step S12. In this embodiment, the second image interpretation knowledge is assumed to be composed of a combination of (i) two data correlations between image feature quantities and image interpretation items and (ii) two data correlations between image interpretation items and disease names. The former is the same as in Embodiment 1, and thus the same description is not repeated here.

The latter is calculated using the method described in "(3) Correlations between Image Interpretation Items and Disease Names". As a result, the correlations in FIG. 18 are obtained.

(Similar Case Search)

The flowchart of a similar case search according to Embodiment 4 of the present disclosure is basically the same as the flowchart of FIG. 19 related to Embodiment 1. The operations in Steps S30 to S34 and Steps S36 to S38 are the same as those in Embodiment 1, and thus the same descriptions are not repeated here.

Figure 36:
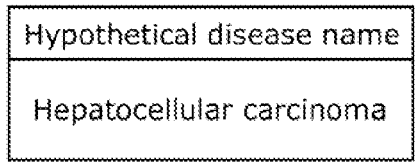
FIG. 36 is a table (a display format) of a disease name hypothetically determined based on the selected image interpretation item according to Embodiment 4 of the present disclosure.

In Step S35, a user input of a selection selected from among the image interpretation item candidates displayed in Step S34 is received via the image interpretation item selecting unit 180. The user input is received so that the image interpretation item selected by the user is used as a similarity measurement (viewpoint) in a similar case search. Image interpretation items having a high fitting degree are displayed on the image interpretation item candidate display and selection area 310 on the display screen, for example, in the form of the table of FIG. 25. The user selects and inputs the target image interpretation item on the display screen by clicking the character string indicating the target image interpretation item using the mouse. FIG. 33 shows an example of the selected image interpretation item. In FIG. 33, the selected image interpretation items "Early stain" and "Washout" are highlighted. Next, with reference to the correlation table of the correlations between the image interpretation items and the disease names in FIG. 18, the image interpretation item candidate display unit 170 obtains (i) the correlations (log-likelihood ratios) with the image interpretation item "Early stain" and all the disease names and (ii) the correlations (log-likelihood ratios) with the image interpretation item "Washout" and all the disease names. The image interpretation item candidate display unit 170 calculates, for each of the disease names, the sum of the correlation between the disease name and the selected image interpretation item "Early stain" and the correlation between the disease name and the selected image interpretation item "Washout". The image interpretation item candidate display unit 170 handles a current disease name having higher correlations with the selected image interpretation items "Early stain" and "Washout" as the sum of the correlations is greater, and presents to the user a display of the disease name having the highest sum of the correlations in the form of the table of FIG. 36. For example, the hepatocellular carcinoma is displayed as the disease name having the highest correlation with the currently being selected one of the image interpretation items.

In this way, the user can recognize which one of the diseases corresponds to the current interpretation target image based on the image interpretation items selected by himself/herself, and takes into account this presented disease name both in the selection of (the) image interpretation items and in the diagnosis of the disease.

Embodiment 5

Next, Embodiment 5 is described. Embodiment 5 is different from Embodiment 1 in that a similar case searching apparatus calculates the fitting degrees with respect to image interpretation items, automatically sets some of the image interpretation items based on the calculated fitting degrees without requiring a user to select the image interpretation items, calculates the weights from the automatically set image interpretation items, and searches out a similar case. These differences from Embodiment 1 are focused in the descriptions given below.

Figure 37:
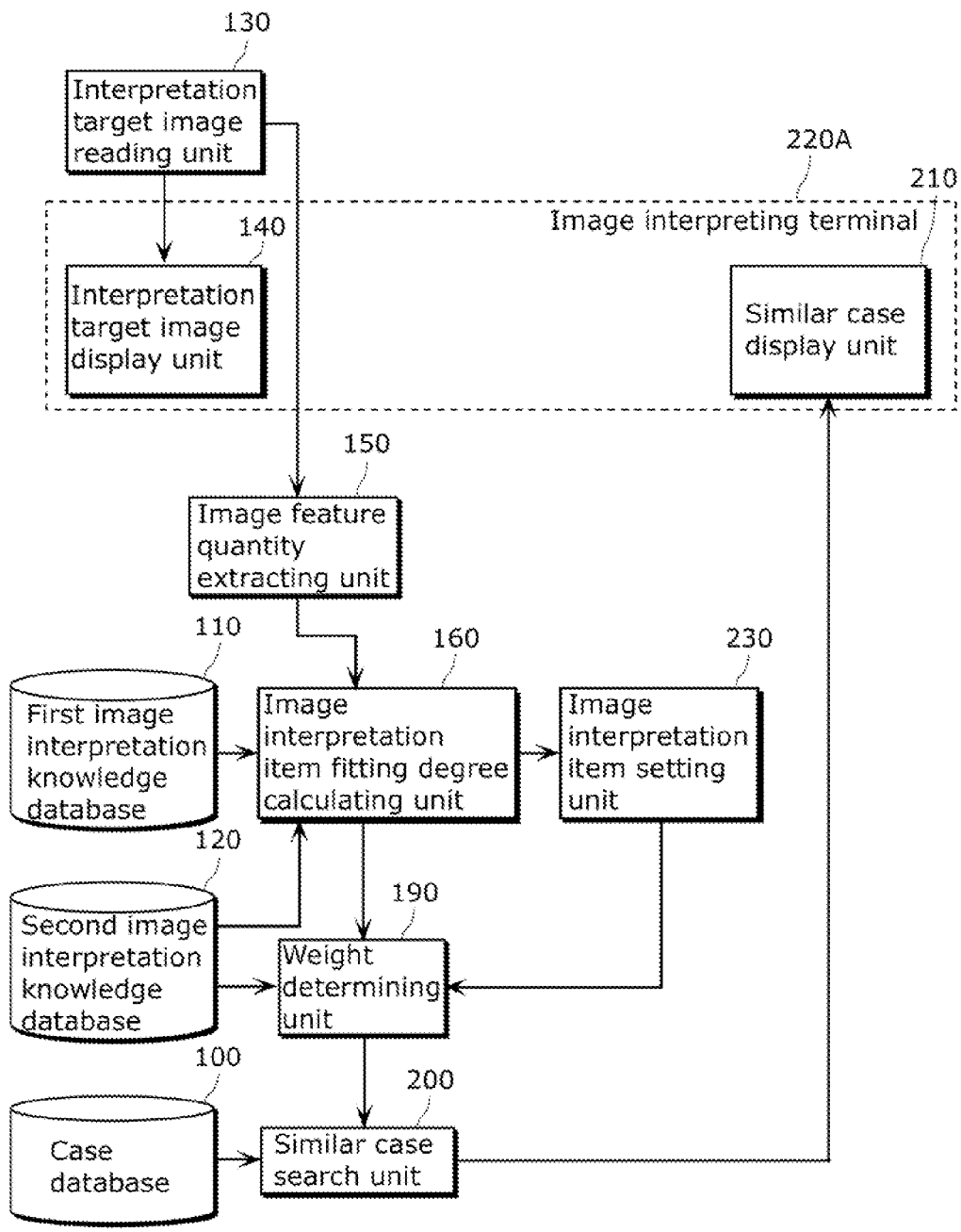
FIG. 37 is a block diagram of a structure of a similar case searching apparatus according to Embodiment 5 of the present disclosure.

FIG. 37 is a block diagram of the structure of a similar case searching apparatus according to Embodiment 5 of the present disclosure. The same structural elements as in FIG. 1 are not explained here again. The similar case searching apparatus according to Embodiment 5 further describes an image interpretation item setting unit 230. The image interpretation item setting unit 230 sets image interpretation items to be used in a similar case search, using, as inputs, the fitting degrees with respect to all the image interpretation items calculated by the image interpretation item fitting degree calculating unit 160. The weight determining unit 190 calculates the weights to image feature quantities in the similar case search, based on the image interpretation items set by the image interpretation item setting unit 230.

In addition, an image interpreting terminal 220A is used instead of the image interpreting terminal 220. The image interpreting terminal 220A comprises an interpretation target image display unit 140 and a similar case display unit 210.
(Preparation of Image Interpretation Knowledge Database)

The flowchart of generating an image interpretation knowledge database for a similar case searching apparatus according to Embodiment 5 of the present disclosure is basically the same as the flowchart of FIG. 2 related to Embodiment 1. The operations performed here are the same as those in Embodiment 1, and thus the same descriptions are not repeated here.

(Similar Case Search)

Figure 38:
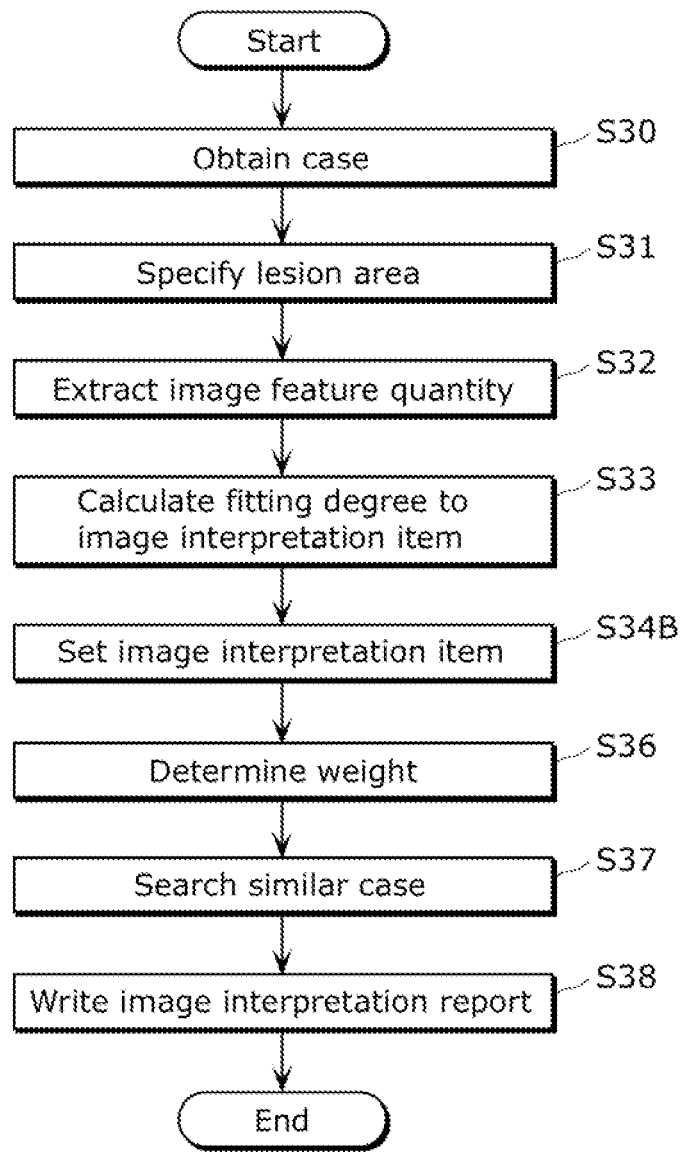
FIG. 38 is a flowchart of a procedure for searching a similar case according to Embodiment 5.

FIG. 38 is a flowchart of a similar case search performed by the similar case searching apparatus according to Embodiment 5 of the present disclosure. The operations in Steps S30 to S33 are the same as those in Embodiment 1, and thus the same descriptions are not repeated here.

In Step S34B, the image interpretation item setting unit 230 sets image interpretation items whose fitting degrees are the bases for the calculations of the weights assigned to image feature quantities in the similar case search, among the fitting degrees with respect to an NII number of image interpretation items calculated in Step S33. Here, the image interpretation item setting unit 230 selects and sets the image interpretation items having a fitting degree greater than or equal to a predetermined threshold value. Here, it is also good to set a predetermined number of image interpretation items in the descending order of their fitting degrees.

In Step S36, all the image interpretation items selected and set are handled equally, and assigned with weights calculated according to Expression 8. Alternatively, it is possible to assign a weight to each pair of the image interpretation items of a kind using the fitting degree set according to Expression 9. The processes in Steps S36 to S38 are the same as in Embodiment 1, and thus the same detailed descriptions are not repeated here.

In this way, the user can execute a similar case search using optimized weights to image feature quantities according to the details of a current interpretation target image without selecting the image interpretation items.

In addition, it is also good to present, to the user, which one or more of image interpretation items are currently being focused in the current similar case search by displaying the image interpretation items set in Step S34B in the form of the table of FIG. 25. Furthermore, it is also good to present the fitting degrees as in FIG. 27. Moreover, it is also good to execute a second similar case search with reference to the result of the current similar case search, by allowing the user to select one or more of the presented image interpretation items.

Embodiment 6

Next, Embodiment 6 is described. Unlike Embodiment 5, Embodiment 6 sets image interpretation items using selection history information of the image interpretation items instead of automatically setting image interpretation items based on the fitting degrees thereof. These differences from Embodiment 1 and Embodiment 5 are focused in the descriptions given below.

Figure 39:
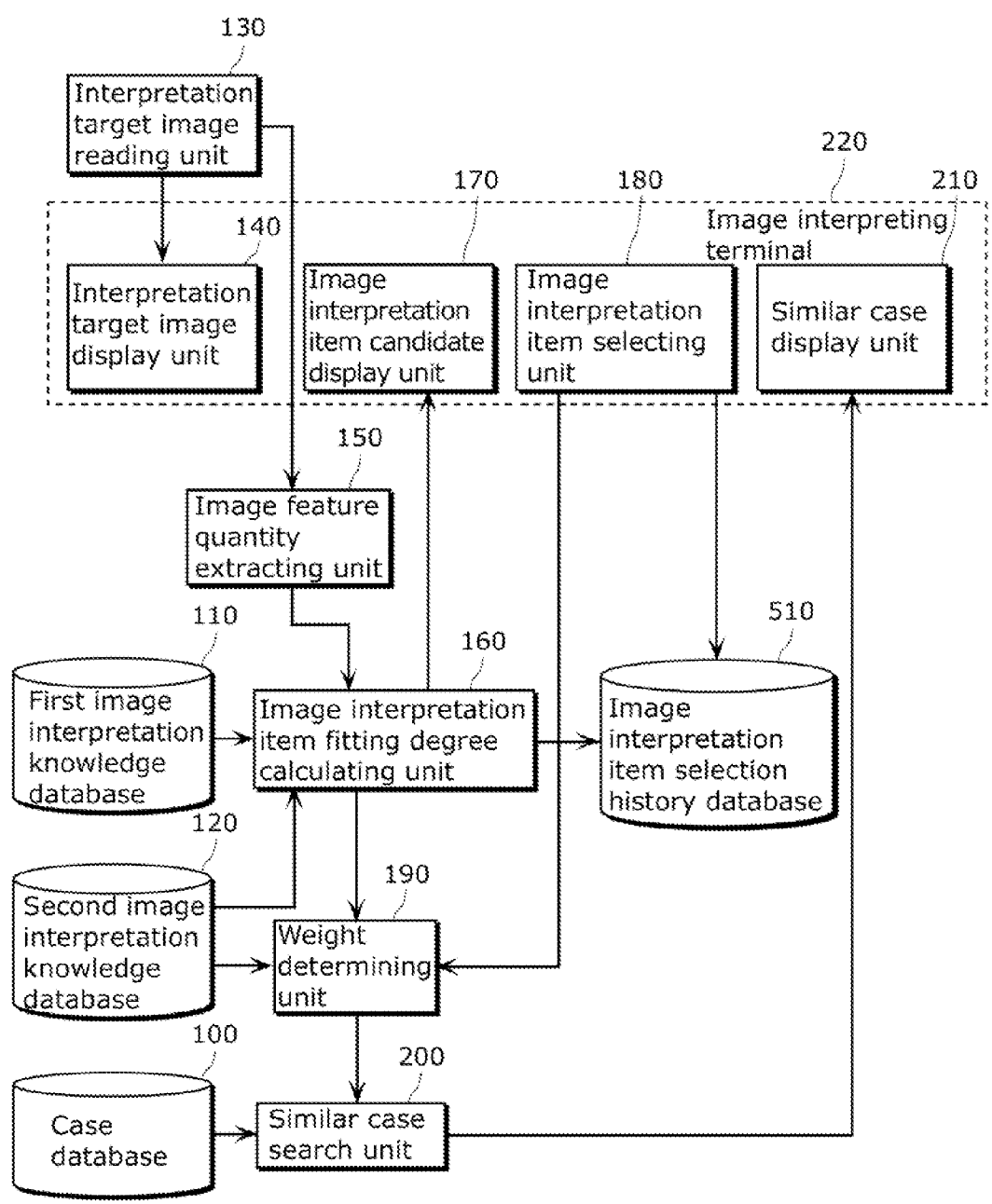
FIG. 39 is a block diagram of a structure of a first similar case searching apparatus according to Embodiment 6 of the present disclosure.
Figure 40:
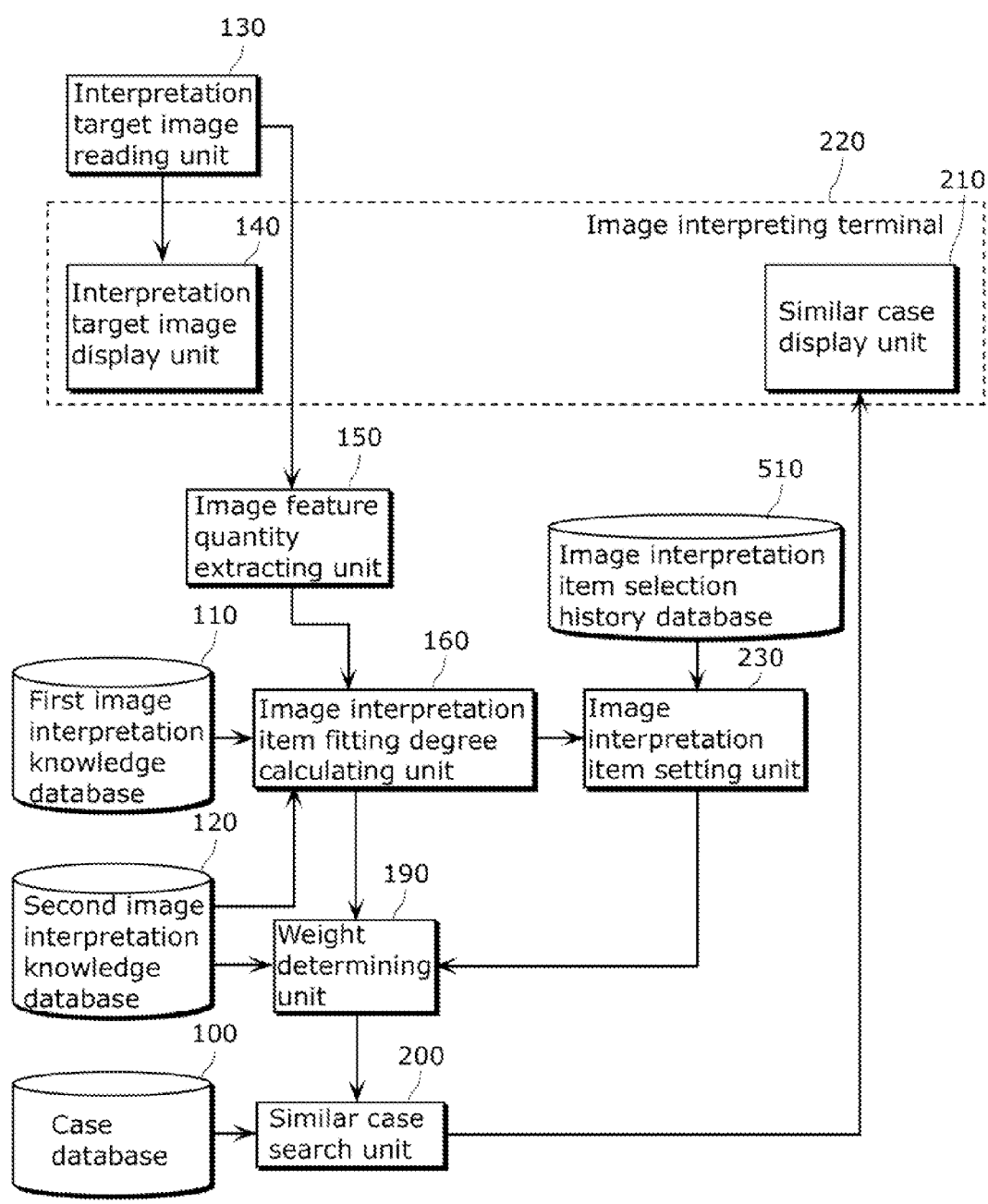
FIG. 40 is a block diagram of a structure of a second similar case searching apparatus according to Embodiment 6.
Figure 42:
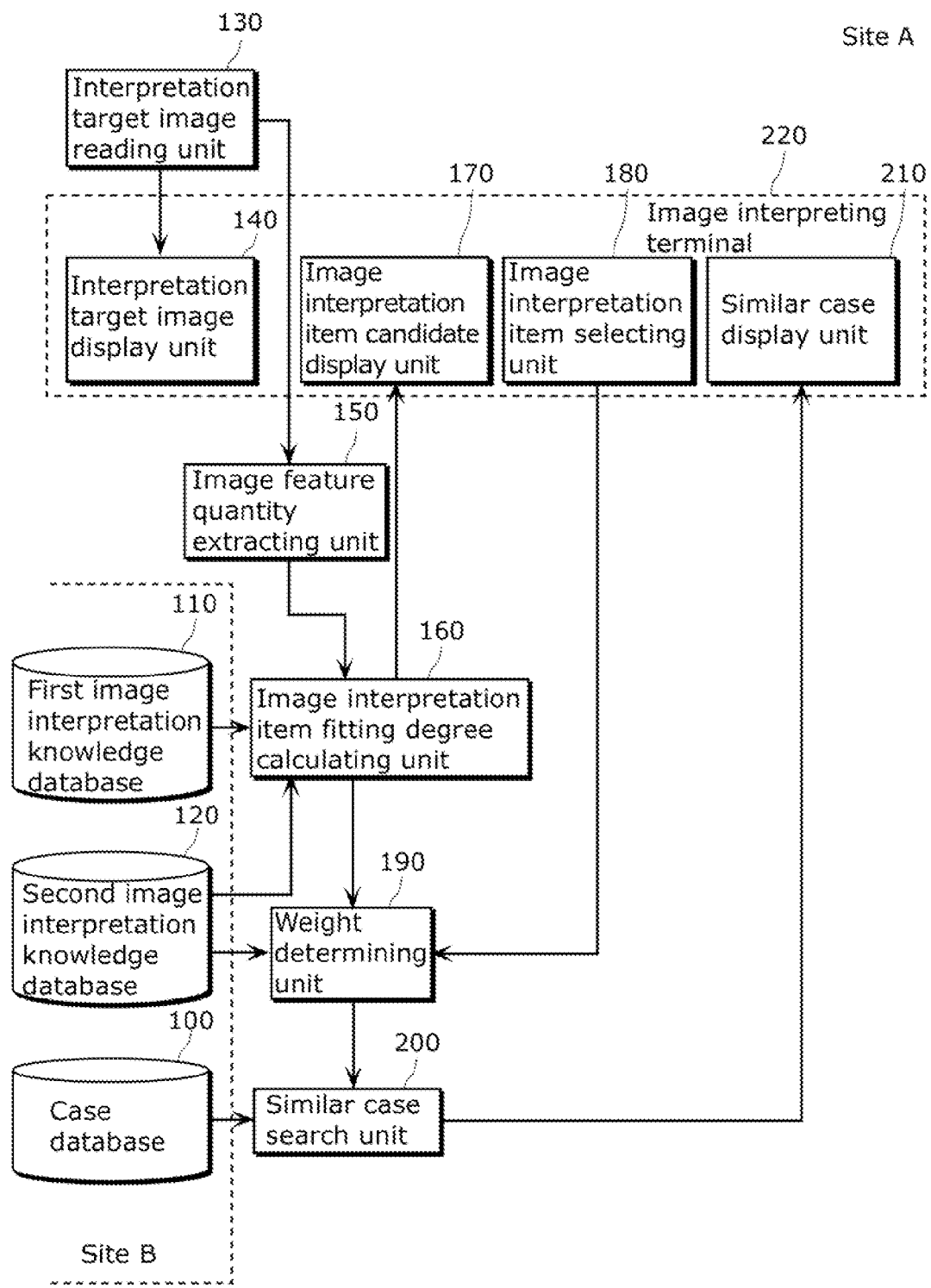
FIG. 42 is a block diagram of another structure of a similar case searching apparatus according to a variation of the present disclosure.

FIG. 39 is a block diagram of the structure of a similar case searching apparatus according to Embodiment 6 of the present disclosure, and FIG. 40 is a block diagram of a modified structure of the same. The same structural elements as those of the similar case searching apparatus shown in FIG. 1 and FIG. 37 are not explained here again. The similar case searching apparatus shown in FIG. 39 is used to generate the selection history information of the image interpretation items. The similar case searching apparatus shown in FIG. 40 automatically sets the image interpretation items using the selection history information of the image interpretation items, and the set image interpretation items are used in a similar case search. Hereinafter, the similar case searching apparatus shown in FIG. 39 is referred to as a first similar case searching apparatus, and the similar case searching apparatus shown in FIG. 40 is referred to as a second similar case searching apparatus.

The first similar case searching apparatus shown in FIG. 39 comprises an image interpretation item selection history database 510, in addition to the structural elements of the similar case searching apparatus shown in FIG. 1. The image interpretation item fitting degree calculating unit 160 writes information about image interpretation items having a high fitting degree and the order of their fitting degrees displayed by the image interpretation item candidate display unit 170. In addition, the image interpretation item selecting unit 180 writes the information about the selected image interpretation items into the image interpretation item selection history database 510.

FIG. 41 is a table of an example of selection history information of image interpretation items stored in the image interpretation item selection history database 510. The selection history information includes: image interpretation items displayed by the image interpretation item candidate display unit 170; the order of the fitting degrees calculated by the image interpretation item fitting degree calculating unit 160; and a selection flag indicating whether or not a selection input is already received by the image interpretation item selecting unit 180. A selection flag having a value of 1 shows that the image interpretation item selecting unit 180 already receives an input of a selected image interpretation item, whereas a selection flag having a value of 0 shows that the image interpretation item selecting unit 180 does not yet receive an input of a selected image interpretation item. FIG. 41 shows selection history information in which the image interpretation items that are "Early stain" and "Washout" are selected. This selection history information shows that the image interpretation items including the selected two image interpretation items were displayed as shown in FIG. 33.

The second similar case searching apparatus shown in FIG. 40 comprises an image interpretation item selection history database 510, in addition to the structural elements of the similar case searching apparatus shown in FIG. 37. With reference to the image interpretation item selection history database 510, the image interpretation item setting unit 230 selects and sets image interpretation items to be used in a similar case search from among image interpretation items calculated by the image interpretation item fitting degree calculating unit 160. These image interpretation items are (i) image interpretation items having a fitting degree greater than or equal to a predetermined threshold value or (ii) a predetermined number of image interpretation items selected in the descending order of their fitting degrees. The processes performed by the image interpretation item setting unit 230 are described in detail later.

(Preparation of Image Interpretation Knowledge Database)

The flowchart of generating an image interpretation knowledge database for the first similar case searching apparatus and the second similar case searching apparatus according to Embodiment 5 of the present disclosure is basically the same as the flowchart of FIG. 2 related to Embodiment 1. The operations performed here are the same as those in Embodiment 1, and thus the same descriptions are not repeated here.

(Similar Case Search)

The flowchart of a similar case search performed by the first similar case searching apparatus according to Embodiment 6 of the present disclosure is the same as in FIG. 19 related to Embodiment 1. However, the following processes are additionally executed.

First, in Step S33, the image interpretation item fitting degree calculating unit 160 writes, into the image interpretation item selection history database 510, information about (i) the image interpretation items having the high fitting degree greater than or equal to the predetermined threshold value or (ii) the predetermined number of image interpretation items selected in the descending order of their fitting degrees, and information about the order of their fitting degrees.

In addition, in Step S35, the image interpretation item selecting unit 180 writes the information about the selected image interpretation items into the image interpretation item selection history database 510.

The flowchart of a similar case search performed by the second similar case searching apparatus according to Embodiment 6 of the present disclosure is the same as in FIG. 38 related to Embodiment 5. However, the process of setting the image interpretation items in Step S34B is different from the flowchart of Embodiment 5.

More specifically, in Step S34B, with reference to the image interpretation item selection history database 510, the image interpretation item setting unit 230 selects and sets image interpretation items to be used in a similar case search from among image interpretation items calculated by the image interpretation item fitting degree calculating unit 160. These image interpretation items are (i) the image interpretation items having the fitting degree greater than or equal to the predetermined threshold value or (ii) the predetermined number of image interpretation items selected in the descending order of their fitting degrees. In other words, the image interpretation item setting unit 230 searches the image interpretation item selection history database 510 for a selection history information item including a combination of image interpretation items that are the same as (i) the image interpretation items having the fitting degree greater than or equal to the predetermined threshold value or (ii) the predetermined number of image interpretation items selected in the descending order of their fitting degrees. The image interpretation item setting unit 230 selects and sets the same image interpretation items as those shown in the searched-out selection history information. For example, when the image interpretation items having a fitting degree greater than or equal to the predetermined threshold value are the five image interpretation items of "Early stain", "Patchy", "Washout", "Homogenous inside", and "Ring-shaped", the image interpretation item fitting degree calculating unit 160 selects and sets the image interpretation items "Early stain" and "Washout", with reference to the selection history information shown in FIG. 41. If plural kinds of selection history information (plural selection patterns in FIG. 41) are possible for the combination of the image interpretation items having the fitting degree greater than or equal to the predetermined threshold value, it is good to select and set the image interpretation items having a highest selection frequency based on the selection history information. Alternatively, it is also good to present, to the user, a predetermined number of kinds of selection history information selected in the descending order of their selection frequencies in the selection history information, so as to allow the user to select one or more of the image interpretation items. For example, the several kinds of selection history information may be classified based on organs or disease names, and the one or more of the image interpretation items may be set using selection history information of the kind classified as being for the target organ or disease name in the similar case search. Here, the target organ or disease name in the similar case search may be input by the user.

According to Embodiment 6, the user can execute a similar case search using optimized weights to image feature quantities according to the details of a current interpretation target image, without selecting the image interpretation items.

In addition, it is also good to present, to the user, which one or more of image interpretation items are currently being focused in the similar case search by displaying the image interpretation items set in Step S34B in the form of the table of FIG. 25. Furthermore, it is also good to present the fitting degrees as in FIG. 27. Moreover, it is also good to execute a second similar case search with reference to the result of the current similar case search, by allowing the user to further select one or more of the presented image interpretation items.

Embodiments 1 to 6 describe examples for searching cases for each of which medical images and an image interpretation report of the medical image are generated. However, search targets in the present disclosure are not limited to the exemplary cases. It is also possible to determine, as search targets, data sets for each of which images and text data of the images are generated. For example, it is also possible to determine, as search targets, data sets for each of which plant images and explanations of the plant images are generated. In this case, it is possible to calculate weights to the image feature quantities focused by the user when preparing explanations of images, by using image feature quantities of the plant images (for example, the number of petals, the width of a stem, or the like) instead of image feature quantities of medical images, and using explanations of the plant images instead of image interpretation report, and search plant images based on the weighted image feature quantities.

As shown in FIG. 31, it is not always necessary that the case database 100, the first image interpretation knowledge database 110, and the second image interpretation knowledge database 120 are included in the similar case search apparatus. In other words, these databases may be provided at a site B different from a site A in which the similar case searching apparatus is present. In this case, the image interpretation item fitting degree calculating unit 160, the weight determining unit 190, and the similar case search unit 200 of the similar case searching apparatus are connected, via a network, to the case database 100, the first image interpretation knowledge database 110, and the second image interpretation knowledge database 120. In addition to these databases, the image interpretation item selection history database 510 shown in FIG. 39 and FIG. 40 does not always need to be provided inside the similar case searching apparatus, and thus may be provided at a site different from the site at which the similar case searching apparatus is present.

In addition, each of the above apparatuses may be configured as, specifically, a computer system including a microprocessor, a ROM, a RAM, a hard disk unit, a display unit, a keyboard, a mouse, and so on. A computer program is stored in the RAM or hard disk unit. The respective apparatuses achieve their functions through the microprocessor's operations according to the computer program. Here, the computer program is configured by combining plural instruction codes indicating instructions for the computer, so as to allow execution of predetermined functions.

Furthermore, a part or all of the structural elements of the respective apparatuses may be configured with a single system-LSI (Large-Scale Integration). The system-LSI is a super-multi-function LSI manufactured by integrating constituent units on a single chip, and is specifically a computer system configured to include a microprocessor, a ROM, a RAM, and so on. A computer program is stored in the RAM. The system-LSI achieves its/their function(s) through the microprocessor's operations according to the computer program.

Furthermore, a part or all of the structural elements constituting the respective apparatuses may be configured as an IC card which can be attached to and detached from the respective apparatuses or as a stand-alone module. The IC card or the module is a computer system configured from a microprocessor, a ROM, a RAM, and so on. The IC card or the module may also be included in the aforementioned super-multi-function LSI. The IC card or the module achieves its/their function(s) through the microprocessor's operations according to the computer program. The IC card or the module may also be implemented to be tamper-resistant.

In addition, the respective apparatuses according to the present disclosure may be realized as methods including the steps corresponding to the unique units of the apparatuses. Furthermore, these methods according to the present disclosure may also be realized as computer programs for executing these methods or digital signals of the computer programs.

In other words, this computer program is a program for causing a computer to execute the steps of the similar case searching method.

Here, the similar case searching method according to an aspect of the present disclosure is a similar case searching method of searching a case database for similar case data items including similar images similar to an interpretation target image, the case database storing a plurality of case data items, and each of the plurality of case data items and a case data item of the interpretation target image including one or more medical images and an image interpretation report that is a document data item indicating interpretations of the medical images, the similar case searching method comprising: extracting a plurality of image feature quantities from one of the medical images that is the interpretation target image; calculating a fitting degree of the image feature quantities extracted in the extracting with respect to each of image interpretation items, based on first image interpretation knowledge composed of information items each indicating a presence range of values of image feature quantities of a corresponding type extracted from medical images whose image interpretation reports include the image interpretation item, each of the image interpretation items being a character string verbally indicating a feature of the medical images, the information items being prepared for the respective image interpretation items, and the values being calculated with respect to each of the image interpretation items; displaying one of (a) image interpretation items each having a fitting degree larger than a predetermined threshold value and (b) a predetermined number of image interpretation items selected in a descending order of their fitting degrees, both (a) and (b) being included in the image interpretation items; allowing a user to select one or more of the image interpretation items displayed in the displaying; determining, based on second image interpretation knowledge, a weight that is added to each of the image feature quantities extracted in the extracting, such that the weight to the image feature quantity is larger as a correlation between the image feature quantity and the one of the image interpretation items selected in the selecting is higher, the second image interpretation knowledge being prepared information defining correlations between image feature quantities extracted from medical images and image interpretation items selected from the image interpretation reports of the medical images; and searching the case database for the similar case data items, by weighting each of the image feature quantities in a first set extracted from the interpretation target image in the extracting and a corresponding one of the image feature quantities in a second set extracted from the medical images included in the case data items registered in the case database, using the weight to the image feature quantity determined in the determining, and comparing the weighted image feature quantities in the first set and the weighted image feature quantities in the second set.

In addition, a similar case searching method according to another aspect of the present disclosure is a similar case searching method of searching a case database for similar case data items including similar images similar to an interpretation target image, the case database storing a plurality of case data items, and each of the plurality of case data items and a case data item of the interpretation target image including one or more medical images and an image interpretation report that is a document data item indicating interpretations of the medical images, the similar case searching method comprising: extracting a plurality of image feature quantities from one of the medical images that is the interpretation target image; calculating a fitting degree of the image feature quantities extracted in the extracting with respect to each of image interpretation items, based on first image interpretation knowledge composed of information items each indicating a presence range of values of image feature quantities of a corresponding type extracted from medical images whose image interpretation reports include the image interpretation item, each of the image interpretation items being a character string verbally indicating a feature of the medical images, the information items being prepared for the respective image interpretation items, and the values being calculated with respect to each of the image interpretation items; setting, as an image interpretation item for use in a similar case search, an image interpretation item having a fitting degree that is a value calculated in the calculating as being larger than or equal to a predetermined threshold value and; determining, based on second image interpretation knowledge, a weight that is added to each of the image feature quantities extracted in the extracting, such that the weight to the image feature quantity is larger as a correlation between the image feature quantity and the one of the image interpretation items selected in the selecting is higher, the second image interpretation knowledge being prepared information defining correlations between image feature quantities extracted from medical images and image interpretation items selected from the image interpretation reports of the medical images; and searching the case database for the similar case data items, by weighting each of the image feature quantities in a first set extracted from the interpretation target image in the extracting and a corresponding one of the image feature quantities in a second set extracted from the medical images included in the case data items registered in the case database, using the weight to the image feature quantity determined in the determining, and comparing the weighted image feature quantities in the first set and the weighted image feature quantities in the second set.

Such computer programs or digital signals according to the present disclosure may be recorded on computer-readable non-volatile recording media such as flexible discs, hard disks, CD-ROMs, MOs, DVDs, DVD-ROMs, DVD-RAMs, BDs (Blu-ray Disc (registered trademark)), and semiconductor memories. In addition, these methods according to the present disclosure may also be realized as the digital signals recorded on these non-volatile recording media.

Furthermore, these methods according to the present disclosure may also be realized as the aforementioned computer programs or digital signals transmitted via a telecommunication line, a wireless or wired communication line, a network represented by the Internet, a data broadcast, and so on.

The apparatuses (or computers or a computer system) according to the present disclosure may also be implemented as a computer system including a microprocessor and a memory, in which the memory stores the aforementioned computer program and the microprocessor operates according to the computer program.

Furthermore, it is also possible to execute another independent computer system by transmitting the programs or the digital signals recorded on the aforementioned non-transitory recording media, or by transmitting the programs or digital signals via the aforementioned network and the like.

Similar case searching apparatus according to one or more aspects of the present disclosure have been described based on the exemplary embodiments. However, these exemplary embodiments do not limit the inventive concept, the scope of which is defined in the appended Claims and their equivalents.

Those skilled in the art will readily appreciate that various modifications may be made in these exemplary embodiments and other embodiments may be made by arbitrarily combining some of the structural elements of different exemplary embodiments without materially departing from the principles and spirit of the inventive concept, the scope of which is defined in the appended Claims and their equivalents.

INDUSTRIAL APPLICABILITY

One or more exemplary embodiments of the present disclosure are applicable to similar case searching apparatus which search and present similar cases provided to doctors for reference, image interpretation training apparatuses for fresh doctors, and the like.

The invention claimed is:

1. A similar case searching apparatus which searches a case database for similar case data items including similar images similar to an interpretation target image, the case database storing a plurality of case data items, and each of the plurality of case data items and a case data item of the interpretation target image including one or more medical images and an image interpretation report that is a document data item indicating interpretations of the medical images, said similar case searching apparatus comprising:
  an image feature quantity extracting unit configured to extract a plurality of image feature quantities from one of the medical images that is the interpretation target image;
  an image interpretation item fitting degree calculating unit configured to calculate a fitting degree of the image feature quantities extracted by said image feature quantity extracting unit with respect to each of image interpretation items, based on first image interpretation knowledge composed of information items each indicating a presence range of values of image feature quantities of a corresponding type extracted from medical images whose image interpretation reports include the image interpretation item, each of the image interpretation items being a character string verbally indicating a feature of the medical images, the information items being prepared for the respective image interpretation items, and the values being calculated with respect to each of the image interpretation items;
  an image interpretation item candidate display unit configured to display one of (a) image interpretation items each having a fitting degree larger than a predetermined threshold value and (b) a predetermined number of image interpretation items selected in a descending order of their fitting degrees, both (a) and (b) being included in the image interpretation items;
  an image interpretation item selecting unit configured to allow a user to select one or more of the image interpretation items displayed by said image interpretation item candidate display unit;
  a weight determining unit configured to determine, based on second image interpretation knowledge, a weight that is added to each of the image feature quantities extracted by said image feature extracting unit, such that the weight to the image feature quantity is larger as a correlation between the image feature quantity and the one of the image interpretation items selected by said image interpretation item selecting unit is higher, the second image interpretation knowledge being prepared information defining correlations between image feature quantities extracted from medical images and image interpretation items selected from the image interpretation reports of the medical images; and a similar case searching unit configured to search the case database for the similar case data items, by weighting each of the image feature quantities in a first set extracted from the interpretation target image by said image feature quantity extracting unit and a corresponding one of the image feature quantities in a second set extracted from the medical images included in the case data items registered in the case database, using the weight to the image feature quantity determined by said weight determining unit, and comparing the weighted image feature quantities in the first set and the weighted image feature quantities in the second set.

2. The similar case searching apparatus according to claim 1, wherein said image interpretation item fitting degree calculating unit is configured to:

obtain, from the first image interpretation knowledge, a presence range information item indicating values of all of the image feature quantities related to each of target image interpretation items with respect to which the fitting degrees are calculated;

calculate matching degrees of the respective image feature quantities extracted by said image feature quantity extracting unit with respect to the obtained presence range information item; and calculate the fitting degree of the image feature quantities extracted by said image feature quantity extracting unit with respect to each of the target image interpretation items, by (i) weighting the image feature quantity using a weight calculated with respect to the matching degree of the image feature quantity such that the weight to the image feature quantity is larger as the image feature quantity is determined, based on the second image interpretation knowledge, to be more highly related to the target image interpretation item, and (ii) integrating the matching degrees calculated for the image feature quantities extracted by said image feature quantity extracting unit.

3. The similar case searching apparatus according to claim 1, wherein said image interpretation item candidate display unit is further configured to display the fitting degrees with respect to the image interpretation items, together with the image interpretation items.

4. The similar case searching apparatus according to claim 1, wherein said image interpretation item candidate display unit is further configured to:

determine a co-occurrence probability of each of pairs of the image interpretation items selected by said image interpretation item selecting unit, based on prepared co-occurrence probability information defining a co-occurrence degree of the pair of the image interpretation items in the image interpretation reports attached to the medical images; and display information indicating a possibility that an inappropriate image interpretation item is included by mistake in one of the pairs having the determined co-occurrence probability when the determined co-occurrence probability is smaller than or equal to a predetermined value.

5. The similar case searching apparatus according to claim 1, wherein said image interpretation item candidate display unit is further configured to display, based on a prepared co-occurrence probability information, information indicating that it is impossible to select the image interpretation item having a co-occurrence probability calculated as being smaller than or equal to the predetermined value with respect to one of the image interpretation items selected by said image interpretation item selecting unit, the prepared co-occurrence probability information defining the co-occurrence degrees of the pairs of the image interpretation items included in the image interpretation reports attached to the medical images.

6. The similar case searching apparatus according to claim 1, wherein said image interpretation item candidate display unit is further configured to:

estimate a disease name having a highest correlation with each of the selected image interpretation items, based on correlation information extracted from the image interpretation reports attached to the medical images, the correlation information being prepared as information defining correlations between disease names and image interpretation items each of which is a character string verbally indicating a feature of medical images; and display the estimated disease name.

7. A similar case searching apparatus which searches a case database for similar case data items including similar images similar to an interpretation target image, the case database storing a plurality of case data items, and each of the plurality of case data items and a case data item of the interpretation target image including one or more medical images and an image interpretation report that is a document data item indicating interpretations of the medical images, said similar case searching apparatus comprising:

an image feature quantity extracting unit configured to extract a plurality of image feature quantities from one of the medical images that is the interpretation target image;

an image interpretation item fitting degree calculating unit configured to calculate a fitting degree of the image feature quantities extracted by said image feature quantity extracting unit with respect to each of image interpretation items, based on first image interpretation knowledge composed of information items each indicating a presence range of values of image feature quantities of a corresponding type extracted from medical images whose image interpretation reports include the image interpretation item, each of the image interpretation items being a character string verbally indicating a feature of the medical images, the information items being prepared for the respective image interpretation items, and the values being calculated with respect to each of the image interpretation items;

an image interpretation item setting unit configured to set, as an image interpretation item for use in a similar case search, an image interpretation item having a fitting degree that is a value calculated by said image interpretation item fitting degree calculating unit as being larger than or equal to a predetermined threshold value and;

a weight determining unit configured to determine, based on second image interpretation knowledge, a weight that is added to each of the image feature quantities extracted by said image feature extracting unit, such that the weight to the image feature quantity is larger as a correlation between the image feature quantity and the one of the image interpretation items set by said image interpretation item setting unit is higher, the second image interpretation knowledge being prepared information defining correlations between image feature quantities extracted from medical images and image interpretation items selected from the image interpretation reports of the medical images;

and a similar case searching unit configured to search the case database for the similar case data items, by weighting each of the image feature quantities in a first set extracted from the interpretation target image by said image feature quantity extracting unit and a corresponding one of the image feature quantities in a second set extracted from the medical images included in the case data items registered in the case database, using the weight to the image feature quantity determined by said weight determining unit, and comparing the weighted image feature quantities in the first set and the weighted image feature quantities in the second set.

8. The similar case searching apparatus according to claim 1, wherein said image interpretation item setting unit is configured to set one or more of the image interpretation items for use in a similar case search, based on history information of image interpretation items previously selected by the user from among the sets of image interpretation items, the one or more of the image interpretation items being obtained by performing the same selection as in the history information from among the image interpretation items having fitting degrees larger than or equal to the predetermined threshold value calculated by said image interpretation item fitting degree calculating unit.

9. A similar case searching method of searching a case database for similar case data items including similar images similar to an interpretation target image, the case database storing a plurality of case data items, and each of the plurality of case data items and a case data item of the interpretation target image including one or more medical images and an image interpretation report that is a document data item indicating interpretations of the medical images, said similar case searching method comprising:

extracting a plurality of image feature quantities from one of the medical images that is the interpretation target image;

calculating a fitting degree of the image feature quantities extracted in said extracting with respect to each of image interpretation items, based on first image interpretation knowledge composed of information items each indicating a presence range of values of image feature quantities of a corresponding type extracted from medical images whose image interpretation reports include the image interpretation item, each of the image interpretation items being a character string verbally indicating a feature of the medical images, the information items being prepared for the respective image interpretation items, and the values being calculated with respect to each of the image interpretation items;

displaying one of (a) image interpretation items each having a fitting degree larger than a predetermined threshold value and (b) a predetermined number of image interpretation items selected in a descending order of their fitting degrees, both (a) and (b) being included in the image interpretation items;

allowing a user to select one or more of the image interpretation items displayed in said displaying;

determining, based on second image interpretation knowledge, a weight that is added to each of the image feature quantities extracted in said extracting, such that the weight to the image feature quantity is larger as a correlation between the image feature quantity and the one of the image interpretation items selected in said selecting is higher, the second image interpretation knowledge being prepared information defining correlations between image feature quantities extracted from medical images and image interpretation items selected from the image interpretation reports of the medical images; and searching the case database for the similar case data items, by weighting each of the image feature quantities in a first set extracted from the interpretation target image in said extracting and a corresponding one of the image feature quantities in a second set extracted from the medical images included in the case data items registered in the case database, using the weight to the image feature quantity determined in said determining, and comparing the weighted image feature quantities in the first set and the weighted image feature quantities in the second set.

10. A similar case searching method of searching a case database for similar case data items including similar images similar to an interpretation target image, the case database storing a plurality of case data items, and each of the plurality of case data items and a case data item of the interpretation target image including one or more medical images and an image interpretation report that is a document data item indicating interpretations of the medical images, said similar case searching method comprising:

extracting a plurality of image feature quantities from one of the medical images that is the interpretation target image;

calculating a fitting degree of the image feature quantities extracted in said extracting with respect to each of image interpretation items, based on first image interpretation knowledge composed of information items each indicating a presence range of values of image feature quantities of a corresponding type extracted from medical images whose image interpretation reports include the image interpretation item, each of the image interpretation items being a character string verbally indicating a feature of the medical images, the information items being prepared for the respective image interpretation items, and the values being calculated with respect to each of the image interpretation items;

setting, as an image interpretation item for use in a similar case search, an image interpretation item having a fitting degree that is a value calculated in said calculating as being larger than or equal to a predetermined threshold value and;

determining, based on second image interpretation knowledge, a weight that is added to each of the image feature quantities extracted in said extracting, such that the weight to the image feature quantity is larger as a correlation between the image feature quantity and the one of the image interpretation items selected in said selecting is higher, the second image interpretation knowledge being prepared information defining correlations between image feature quantities extracted from medical images and image interpretation items selected from the image interpretation reports of the medical images; and searching the case database for the similar case data items, by weighting each of the image feature quantities in a first set extracted from the interpretation target image in said extracting and a corresponding one of the image feature quantities in a second set extracted from the medical images included in the case data items registered in the case database, using the weight to the image feature quantity determined in said determining, and comparing the weighted image feature quantities in the first set and the weighted image feature quantities in the second set.

11. A non-transitory computer-readable recording medium for use in a computer, said recording medium having a computer program recorded thereon for causing the computer to execute the similar case searching method according to claim 9.

12. A non-transitory computer-readable recording medium for use in a computer, said recording medium having a computer program recorded thereon for causing the computer to execute the similar case searching method according to claim 10.

* * * * *